(12) United States Patent
Bocek et al.

(10) Patent No.: US 8,170,662 B2
(45) Date of Patent: May 1, 2012

(54) METHOD AND APPARATUS FOR CHARGING PARTITIONED CAPACITORS

(75) Inventors: Joseph M. Bocek, Seattle, WA (US);
Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 281 days.

(21) Appl. No.: 11/462,301

(22) Filed: Aug. 3, 2006

(65) Prior Publication Data

US 2008/0032473 A1 Feb. 7, 2008

(51) Int. Cl.
*A61N 1/36* (2006.01)

(52) U.S. Cl. .................. 607/4; 607/2; 607/5; 607/7

(58) Field of Classification Search ............... 607/1, 2, 607/4, 5, 7

See application file for complete search history.

(56) References Cited

U.S. PATENT DOCUMENTS

| | | | |
|---|---|---|---|
| 3,010,056 A | 11/1961 | Kurland et al. |
| 3,211,154 A | 10/1965 | Becker et al. |
| 3,643,168 A | 2/1972 | Manicki |
| 3,803,457 A | 4/1974 | Yamamoto |
| 4,001,657 A | 1/1977 | Robinson |
| 4,047,790 A | 9/1977 | Carino |
| 4,088,108 A | 5/1978 | Hager |
| 4,252,575 A | 2/1981 | Bernard |
| 4,352,145 A | 9/1982 | Stockman |
| 4,406,286 A | 9/1983 | Stein |
| 4,539,999 A | 9/1985 | Mans |
| 5,111,816 A | 5/1992 | Pless et al. |
| 5,142,439 A | 8/1992 | Huggett et al. |
| 5,163,427 A | 11/1992 | Keimel |
| 5,199,429 A | 4/1993 | Kroll et al. |
| 5,227,960 A | 7/1993 | Kunishi et al. |
| 5,230,336 A | 7/1993 | Fain et al. |
| 5,334,219 A | 8/1994 | Kroll |

(Continued)

FOREIGN PATENT DOCUMENTS

EP 0510456 A1 10/1992

(Continued)

OTHER PUBLICATIONS

"PCT Application No. PCT/US2007/017537, International Search Report and Written Opinion mailed Jan. 18, 2008", 13 pgs.

(Continued)

*Primary Examiner* — Carl H Layno
*Assistant Examiner* — Jennifer Stewart
(74) *Attorney, Agent, or Firm* — Schwegman, Lundberg & Woessner, P.A.

(57) ABSTRACT

One aspect of this disclosure relates to an apparatus for providing a selective capacitance. An embodiment of the apparatus includes a first and second capacitor in a stack, and a switching circuit connected between the first and second capacitors. The switching circuit has at least two states, and is adapted to provide a first defibrillation capacitance in a first state and a second defibrillation capacitance in a second state. A switching circuit embodiment includes a field effect transistor (FET) adapted to have a source connected to the first capacitor and a drain connected to the second capacitor, a bipolar junction transistor (BJT) adapted to have an emitter connected to the source of the FET and a collector connected to a gate of the FET, a first current source connected to the collector of the BJT, and a second current source connected to a base of the BJT.

23 Claims, 13 Drawing Sheets

U.S. PATENT DOCUMENTS

| | | | |
|---|---|---|---|
| 5,385,575 | A | 1/1995 | Adams |
| 5,411,525 | A | 5/1995 | Swanson et al. |
| 5,413,591 | A | 5/1995 | Knoll |
| 5,484,452 | A * | 1/1996 | Persson ............................ 607/5 |
| 5,493,471 | A | 2/1996 | Walther et al. |
| 5,507,781 | A | 4/1996 | Kroll et al. |
| 5,527,346 | A | 6/1996 | Kroll |
| 5,591,211 | A | 1/1997 | Meltzer |
| 5,634,938 | A | 6/1997 | Swanson et al. |
| 5,658,319 | A | 8/1997 | Kroll |
| 5,720,767 | A | 2/1998 | Amely-Velez |
| 5,749,904 | A | 5/1998 | Gliner et al. |
| 5,827,326 | A | 10/1998 | Kroll et al. |
| 5,836,972 | A | 11/1998 | Stendahl et al. |
| 5,871,505 | A | 2/1999 | Adams et al. |
| 5,902,323 | A | 5/1999 | Brewer et al. |
| 5,905,398 | A | 5/1999 | Todsen et al. |
| 5,908,443 | A | 6/1999 | Brewer et al. |
| 5,930,109 | A | 7/1999 | Fishler |
| 5,948,004 | A | 9/1999 | Weijand et al. |
| 5,968,080 | A | 10/1999 | Brewer et al. |
| 6,047,211 | A | 4/2000 | Swanson et al. |
| 6,047,212 | A | 4/2000 | Gliner et al. |
| 6,091,989 | A | 7/2000 | Swerdlow et al. |
| 6,096,063 | A | 8/2000 | Lopin et al. |
| 6,148,233 | A | 11/2000 | Owen et al. |
| 6,208,896 | B1 | 3/2001 | Mulhauser |
| 6,241,751 | B1 | 6/2001 | Morgan et al. |
| 6,251,124 | B1 | 6/2001 | Youker et al. |
| 6,426,861 | B1 | 7/2002 | Munshi |
| 6,456,877 | B1 | 9/2002 | Fishler |
| 6,480,738 | B2 | 11/2002 | Irnich |
| 6,484,056 | B2 | 11/2002 | Fisher et al. |
| 6,647,290 | B2 | 11/2003 | Wuthrich |
| 6,668,193 | B2 | 12/2003 | Ware et al. |
| 6,714,818 | B1 | 3/2004 | Fishler et al. |
| 6,763,266 | B1 | 7/2004 | Kroll |
| 6,778,860 | B2 | 8/2004 | Ostroff et al. |
| 7,033,406 | B2 | 4/2006 | Weir et al. |
| 7,043,301 | B1 | 5/2006 | Kroll et al. |
| 7,157,671 | B2 | 1/2007 | O'Phelan et al. |
| 7,224,575 | B2 | 5/2007 | Sherwood |
| 7,466,536 | B1 | 12/2008 | Weir et al. |
| 7,499,260 | B2 | 3/2009 | Schott et al. |
| 7,667,954 | B2 | 2/2010 | Lessner et al. |
| 2002/0035380 | A1 | 3/2002 | Rissmann et al. |
| 2002/0049473 | A1 | 4/2002 | Irnich |
| 2002/0161406 | A1* | 10/2002 | Silvian ............................ 607/5 |
| 2003/0055460 | A1 | 3/2003 | Owen et al. |
| 2003/0078620 | A1* | 4/2003 | Waltman ........................... 607/5 |
| 2003/0088279 | A1 | 5/2003 | Rissmann et al. |
| 2003/0216786 | A1* | 11/2003 | Russial ............................ 607/5 |
| 2004/0143297 | A1* | 7/2004 | Ramsey, III ...................... 607/5 |
| 2004/0147960 | A1* | 7/2004 | O'Phelan et al. ................. 607/1 |
| 2005/0021094 | A1 | 1/2005 | Ostroff et al. |
| 2005/0075677 | A1 | 4/2005 | Ganion et al. |
| 2005/0137625 | A1 | 6/2005 | Rissmann et al. |
| 2005/0154423 | A1 | 7/2005 | Goedeke et al. |
| 2005/0264979 | A1 | 12/2005 | Breyen et al. |
| 2006/0023400 | A1 | 2/2006 | Sherwood |
| 2006/0259082 | A1 | 11/2006 | Youker et al. |
| 2007/0162077 | A1 | 7/2007 | Sherwood |
| 2008/0029482 | A1 | 2/2008 | Sherwood |
| 2008/0030927 | A1 | 2/2008 | Sherwood |
| 2008/0208270 | A1 | 8/2008 | Linder et al. |

FOREIGN PATENT DOCUMENTS

| | | |
|---|---|---|
| EP | 0646391 A1 | 4/1995 |
| WO | WO-2005/092436 A1 | 10/2005 |
| WO | WO-2008/019141 A1 | 2/2008 |

OTHER PUBLICATIONS

Block, M., "Biphasic Defibrillation Using a Single Capacitor with Large Capacitance: Reduction of Peak Voltages and ICD Device Size", *PACE*, Vo. 19, (Feb. 1996),207-214.

Block, M., "Internal Defibrillation with Smaller Capacitors: A Prospective Randomized Cross-Over Comparison of Defibrillation Efficacy Obtained with 90-µF and 125-µf Capacitors in Humans", *Journal of Cardiovascular Electrophysiology*, vol. 6, No. 5, (May 1995),333-342.

Brugada, J., "Clinical Evaluation of Defibrillation Efficacy With a New Single-Capacitor Biphasic Waveform in Patients Undergoing Implantation of an Implantable Cardioverter Defibrillator", *The European Society of Cardiology*, vol. 3, (Oct. 2001), 278-284.

Hahn, S. J., et al., "Large Capacitor Defibrillation Waveform Reduces Peak Voltages Without Increasing Energies", *PACE*, 18(Part II), (Jan. 1995), 203-207.

Linder, W. J., et al., "High Voltage Capacitor Route With Integrated Failure Point", U.S. Appl. No. 11/677,793, filed Feb. 22, 2007.

"U.S. Appl. No. 11/462,295 Non-Final Office Action mailed Aug. 21, 2008", 8 pgs.

"U.S. Appl. No. 11/462,281, Non Final Action Mailed Oct. 8, 2008", OARN, 14 pgs.

"U.S. Appl. No. 11/462,281, Response filed Jan. 8, 2009 to Non Final Office Action mailed Oct. 8, 2008", 13 pgs.

"U.S. Appl. No. 11/462,281, Final Office Action mailed Mar. 24, 2009", 9 pgs.

"U.S. Appl. No. 11/462,295, Notice of Allowance mailed Dec. 16, 2008", 7 pgs.

"U.S. Appl. No. 11/462,295, Response filed Nov. 18, 2008 to Non Final Office Action mailed Aug. 21, 2008", 14 pgs.

"U.S. Appl. No. 11/462,295, Notice of Allowance mailed Apr. 7, 2009", 6 pgs.

"U.S. Appl. No. 11/182,707, Non-Final Office Action mailed Feb. 24, 2006", 15 pgs.

"U.S. Appl. No. 11/182,707, Notice of Allowance mailed Nov. 16, 2006", 7 pgs.

"U.S. Appl. No. 11/182,707, Response filed Aug. 24, 2006 to Non-Final Office Action mailed Feb. 24, 2006", 9 pgs.

"U.S. Appl. No. 11/182,707, Supplemental Notice of Allowance mailed Feb. 12, 2007", 5 pgs.

"U.S. Appl. No. 11/462,281, Non Final Office Action Mailed Oct. 1, 2009", 12 pgs.

"U.S. Appl. No. 11/462,281, Response filed Dec. 29, 2009 to Non Final Office Action mailed Oct. 1, 2009", 11 pgs.

"U.S. Appl. No. 11/462,281, Responsse filed Aug. 24, 2009 to Final Office Action mailed Mar. 24, 2009", 8 pgs.

"U.S. Appl. No. 11/462,295, Notice of Allowance mailed Jul. 27, 2009", 6 pgs.

"U.S. Appl. No. 11/684,914, Non-Final Office Action mailed Jul. 8, 2009", 19 pgs.

"U.S. Appl. No. 11/462,281, Final Office Action mailed Apr. 1, 2010", 12 pgs.

"U.S. Appl. No. 11/462,295, Non-Final Office Action mailed Feb. 19, 2010", 9 pgs.

"U.S. Appl. No. 11/462,295, Response filed Jun. 21, 2010 to Non Final Office Action mailed Feb. 19, 2010", 11 pgs.

"U.S. Appl. No. 11/684,914, Final Office Action mailed Mar. 8, 2010", 20 pgs.

"U.S. Appl. No. 11/684,914, Response filed Jan. 7, 2010 to Non Final Office Action mailed Jul. 8, 2009", 20 pgs.

"Electrolytic Capacitors", *Electrochemistry Encyclopedia*, [online]. http://electrochem.cwru.edu/encycl/art-c04-electr-cap.htm, (Mar. 2005), 10 pgs.

"U.S. Appl. No. 11/462,281, Non-Final Office Action mailed Aug. 19, 2010", 11 pgs.

"U.S. Appl. No. 11/462,281, Response filed Jun. 30, 2010 to Final Office Action mailed Apr. 1, 2010", 9 pgs.

"U.S. Appl. No. 11/462,281, Response filed Dec. 12, 2010 to Non-Final Office Action mailed Aug. 19, 2010", 13 pgs.

"U.S. Appl. No. 11/462,295, Final Office Action mailed Sep. 17, 2010", 8 pgs.

"U.S. Appl. No. 11/462,295, Response filed Jan. 11, 2011 to Final Office Action mailed Sep. 17, 2010", 9 pgs.

"U.S. Appl. No. 11/684,914, Examiner Interview Summary received May 5, 2010", 3 pgs.

"U.S. Appl. No. 11/684,914, Non-Final Office Action mailed Sep. 27, 2010", 20 pgs.

"U.S. Appl. No. 11/684,914, Non-Final Office Action mailed Dec. 16, 2010", 20 pgs.

"U.S. Appl. No. 11/684,914, Response filed Sep. 8, 2010 to Final Office Action mailed Mar. 8, 2010", 11 pgs.

"Ref-06, Energy Stored in a Capacitor," (Apr. 2000).

"U.S. Appl. No. 11/462,281, Final Office Action mailed Mar. 21, 2011", 15 pgs.

"U.S. Appl. No. 11/462,295, Non-Final Office Action mailed Apr. 5, 2011", 9 pgs.

"U.S. Appl. No. 11/684,914, Response filed Jun. 15, 2011 to Non-Final Office Action mailed Dec. 16, 2010", 14 pgs.

"U.S. Appl. No. 11/462,281, Response filed Sep. 15, 2011 to Final Office Action mailed Mar. 21, 2011", 11 pgs.

"U.S. Appl. No. 11/462,295, Response filed Sep. 15, 2011 to Non-Final Office Action mailed Apr. 5, 2011", 10 pgs.

"U.S. Appl. No. 11/684,914, Examiner Interview Summary mailed Oct. 14, 2011", 3 pgs.

"U.S. Appl. No. 11/684,914, Final Office Action mailed Jul. 19, 2011", 20 pgs.

"U.S. Appl. No. 11/684,914, Notice of Allowance mailed Nov. 14, 2011", 7 pgs.

"U.S. Appl. No. 11/684,914, Response filed Oct. 18, 2011 to Final Office Action mailed Jul. 19, 2011", 14 pgs.

* cited by examiner

METHOD AND APPARATUS FOR CHARGING PARTITIONED CAPACITORS

CROSS REFERENCE TO RELATED APPLICATIONS

The following commonly assigned U.S. patent application is related to the present application and is incorporated herein by reference in its entirety: "METHOD AND APPARATUS FOR HIGH VOLTAGE ALUMINUM CAPACITOR DESIGN," Ser. No. 11/182,707, filed on Jul. 15, 2005. The following U.S. patent applications, which are commonly assigned and filed even date herewith, are incorporated by reference: "Method and Apparatus for Selectable Energy Storage Implantable Cardioverter Defibrillator," Ser. No. 11/462,281; "Method and Apparatus for Partitioned Capacitor," Ser. No. 11/462,295.

TECHNICAL FIELD

This disclosure relates generally to electrical energy storage, and more particularly to methods and apparatuses including a selectable energy storage implantable cardioverter defibrillator.

BACKGROUND

Various electrical devices using capacitors are in production. Cameras, cardiac rhythm management devices and other devices use capacitors to provide one or more pulses of electrical energy. But conventional capacitor designs and capacitor manufacturing problems have limited the way capacitors are used.

For example, one problem facing device manufacturers is how to providing a range of capacitances and energy levels which can be used in a device. Existing designs have yet to provide a capacitor which is adjustable without sacrificing packaging space, weight and manufacturing simplicity.

Another problem facing manufacturers of implantable devices is how to provide a device which has a capacitance and energy level which selected based on an impedance which is in turn based on the nature of an implantation. Existing capacitor designs are able to provide a single capacitance and energy level. This is especially problematic in the defibrillation arts, which would benefit from a capacitor which provides capacitance and energy in a manner tailored for a specific use.

At the device level, there exist problems in providing an efficient electrical device design to provide for a variety of capacitances. New circuit designs are needed which can provide multiple capacitances and energy levels.

SUMMARY

The above-mentioned problems and others not expressly discussed herein are addressed by the present subject matter and will be understood by reading and studying this specification.

Disclosed herein, among other things, is an apparatus for charging and discharging partitioned capacitors. One embodiment of the apparatus includes multiple capacitive elements and a switching circuit connected between the capacitive elements. According to various embodiments, the switching circuit is adapted to programmably connect a plurality of the capacitive elements to provide a desired defibrillation capacitance. The switching circuit is adapted to programmably connect a plurality of the capacitive elements to selectively charge connected elements for use in a defibrillator, according to various embodiments.

Another embodiment of the apparatus includes a first and second capacitor in a stack, the first and second capacitors including a plurality of substantially planar electrodes. The apparatus embodiment also includes a switching circuit connected between the first and second capacitors. The switching circuit has at least two states, and is adapted to provide a first defibrillation capacitance in a first state and a second defibrillation capacitance in a second state, according to various embodiments.

A further embodiment of the apparatus includes a first and second capacitor in a stack, the first and second capacitors including a plurality of substantially planar electrodes. The apparatus embodiment also includes a switching circuit connected between the first and second capacitors. In this embodiment, the switching circuit includes a field effect transistor (FET) adapted to have a source connected to the first capacitor and a drain connected to the second capacitor, a bipolar junction transistor (BJT) adapted to have an emitter connected to the source of the FET and a collector connected to a gate of the FET, a first current source connected to the collector of the BJT, and a second current source connected to a base of the BJT. According to various embodiments, activating the first current source turns the FET on, connecting the first and second capacitors, and activating the second current source turns the FET off, isolating the first and second capacitors.

One aspect of this disclosure relates to a method for making an apparatus with a variable defibrillation capacitance. According to an embodiment of the method, a first and second capacitor are formed in a stack, the first and second capacitors including a plurality of substantially planar electrodes, and a switching circuit is connected between the first and second capacitors. The switching circuit includes a first and second state, and selecting the first state selects the first and second capacitor to provide a defibrillation capacitance. Selecting the second state selects the first capacitor to provide a defibrillation capacitance, according to various embodiments.

One aspect of this disclosure relates to a method for making an apparatus for charging partitioned capacitors. According to an embodiment of the method, a first and second capacitor are formed in a stack, the first and second capacitors including a plurality of substantially planar electrodes, and a switching circuit is connected between the first and second capacitors. The switching circuit includes a field effect transistor (FET) connected between the first and second capacitors, a bipolar junction transistor (BJT) connected between a gate and source of the FET, a first current source connected to the gate of the FET, and a second current source connected to a base of the BJT. Selectively activating the first current source turns the FET on, connecting the first and second capacitors, and selectively activating the second current source turns the FET off, isolating the first and second capacitors according to various embodiments.

One aspect of this disclosure relates to a method for combining or isolating multiple capacitors within a capacitor stack. An embodiment of the method includes forming a first and second capacitor in a stack, the first and second capacitors including a plurality of substantially planar electrodes. The method embodiment also includes selecting the first capacitor and the second capacitor by activating a first electrical source and selecting the first capacitor by activating a second electrical source. According to various embodiments, the first electrical source and the second electrical source include a current source.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter relates to capacitors. In various embodiments, the present subject matter includes one or more capacitors including a plurality of substantially planar electrodes. In various embodiments, these substantially planar electrodes are in a stack. In some embodiments, the stack is plate shaped and as such, defines a flat capacitor. Capacitors of the present subject matter include anodic elements and cathodic elements. The present subject matter additionally includes capacitors using electrolyte.

Figure 1:
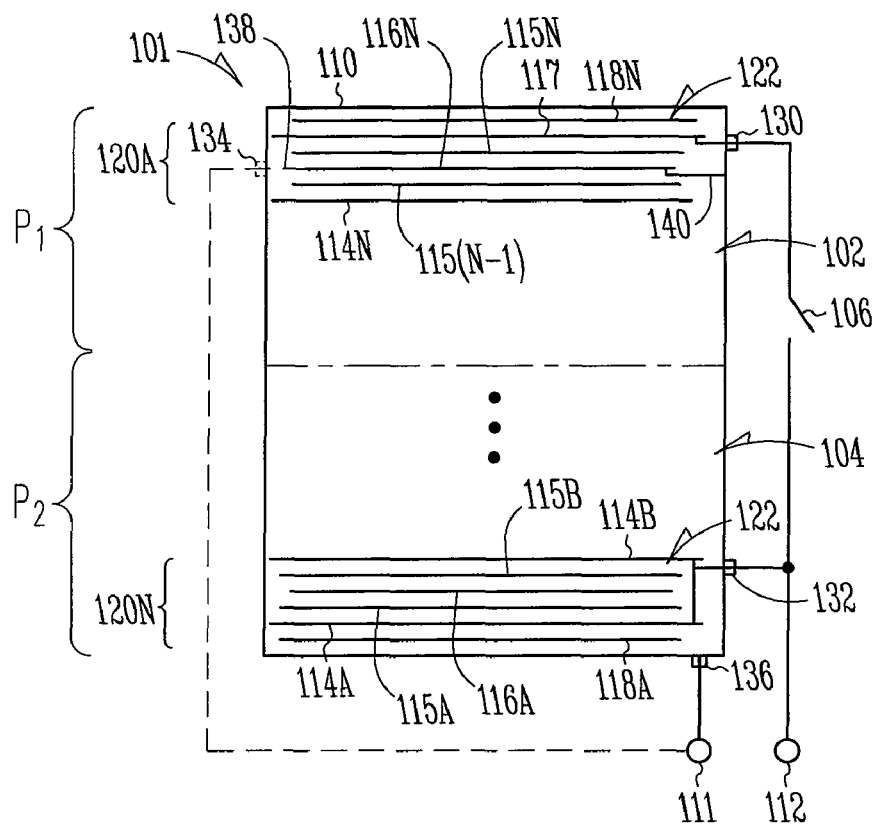
FIG. 1 shows a schematic of a power source including a first and second capacitor subset, according to one embodiment of the present subject matter.

FIG. 1 shows a schematic of a power source including a first 102 and second 104 capacitor subset, according to one embodiment of the present subject matter. The power source 101 includes a case 110. Positioned inside the case 110, in various embodiments, is a stack 122 of substantially planar capacitor electrodes. Some embodiments use foil shaped electrodes. In various embodiments, the stack 122 includes cathodes and anodes. In some embodiments, case 110 is manufactured from a conductive material, such as aluminum. Stainless steel, titanium, or combinations thereof are used in optional embodiments. These materials are not an exhaustive or exclusive list, as other materials work with the present subject matter. For example, in additional embodiments, the case is manufactured using a nonconductive material, such as ceramic or plastic. The first 102 and second 104 capacitor subset store charge independently, in various embodiments.

In various embodiments, the case 110 includes one or more case portions. In various embodiments, the one or more case portions are connected to one another. In various embodiments, connected case portions are also connected to a seal which seals the case portions to one another. In various embodiments, the seal is a hermetic seal. In various embodiments, a seal can include a cured resin. In additional embodiments, a seal can include a weld. Some embodiments of the present subject matter include a cured resin which resists the flow of electrolyte. Some of these embodiments allow for the passage of gas molecules. Some embodiments of the present subject matter include a seal adapted to allow the passage of hydrogen atoms. Some of these embodiments include cured epoxy resin.

Various embodiments dispose electrolyte in the case 110. In some embodiments, the electrolyte is fluidic in use. Some embodiments includes an electrolyte which substantially files interstices in the case.

In various embodiments, power source 101 includes a first terminal 130 and a second terminal 132 for connecting capacitor stack 122 to an outside electrical component. In some embodiments where case 110 is conductive, first terminal 130 and second terminal 132 are feedthroughs sealed to the case and electrically insulated from the case 110. Some embodiments include epoxy seals. The capacitor incorporates additional connection structures and methods in additional embodiments. The present subject matter includes, but is not limited to, additional embodiments disclosed on pages 12-13, 59-60, 63-82 of related and commonly assigned Provisional U.S. patent application: "Method and Apparatus for Single High Voltage Aluminum Capacitor Design," Ser. No. 60/588,905, filed on Jul. 16, 2004, incorporated herein by reference.

In various embodiments, electrodes of the stack 122 are connected to the case 110. For example, in some embodiments, cathodes 116A-N of the stack are connected to the case 110. Cathodes 116A-N can be connected with a single mechanical connection 140, or multiple mechanical connections, in various embodiments. In some embodiments including multiple cathode layers which are electrically isolated from one another, the cathodes are interconnected in the case 110.

In some embodiments, the cathodes 116A-N are not connected to the case, but are instead routed out of the case through a third terminal 134. In some embodiments, the third terminal 134 is a feedthrough sealed to case 110. In additional embodiments, the third terminal is electrically insulated from the case 110. Additional embodiments within the present subject matter connect one or more anode layers to the case 110, and route the cathodes outside of the case 110 using terminals.

Capacitor stack 122 includes one or more cathode layers 116A-N, one or more separator layers 115A-N, and one or more anode layers 114A-N, in various embodiments. In some embodiments, these components are stacked sequentially from the top of a stack to the bottom of a stack. The illustrated embodiment shows anode layers 114A-N which overhang cathode layers 116A-N. It should be noted that this configuration is only one of the configurations possible within the scope of the present subject matter, and additional embodiments include configurations in which there is no overhang. Separator layers 115A-N overhang electrodes in some embodiments of the present subject matter, and do not overhang electrodes in additional embodiments of the present subject matter.

Additionally, in some embodiments, capacitor subcomponents are organized into capacitor elements 120A-N. An example element includes an anode layer, a first separator layer, a cathode layer, and a second separator layers, although elements including other subcomponent configurations are within the scope of the present subject matter.

In various embodiments, stack 122 is formed in two steps, including a first step of stacking capacitor components into two or more elements 120A-N, and a second step of stacking elements 120A-N into a stack. Various embodiment of the present subject matter include, but are not limited to, configurations disclosed on pages 41-50 of related and commonly assigned copending Provisional U.S. Patent Publication: "Method and Apparatus for Single High Voltage Aluminum Capacitor Design," Ser. No. 60/588,905, filed on Jul. 16, 2004, incorporated herein by reference.

Various embodiments of the present subject matter include one or more cathode layers. In various embodiments, at least one of the cathode layers 116A-N is metallic. Some embodiments use aluminum, tantalum, hafnium, niobium, titanium, zirconium, or combinations of these metals. Some embodiments use an aluminum substrate coated in titanium. Some embodiments including a titanium coating have an additional oxide coating. In various embodiments, multiple cathode layers in a stack are interconnected.

Embodiments of the present subject matter include a third anode layer in the stack, and include a fourth terminal. A fourth terminal, in various embodiments, is sealed to the case. Some embodiments include a feedthrough for routing the third anode through the case. A third anode may additionally be connected to anodes of the stack 122 with a switch, as disclosed herein. Other anodes and partitions, including partitions greater than three, are contemplated by the present subject matter.

Interconnected layers can be interconnected using a variety of methods and structures which include: welding the cathode layers to each other; welding the cathode layers to each other using a filler metal; and welding an interconnection member to each layer. The presently disclosed connections are not exhaustive or exclusive of the present subject matter; additional connections fall within the present scope.

Some embodiments including a titanium coated cathode material have a higher capacitance per unit area than traditional aluminum electrolytic capacitor cathodes. Traditional cathodes which are 98% aluminum purity or higher generally have capacitance per unit area of approximately 250 uF/cm$^2$ for 30 micron thick cathode, with an oxide breakdown voltage in the 1-3 volt range. However, a cathode as described above results in a capacitance per unit area which, in some embodiments, is as high as 1000 uF/cm$^2$ or more.

Advantageously, this provides a single cathode which services an anode without exceeding the oxide breakdown voltage. When using a traditional cathode to service several layers (2 or more) of anode, the cathode voltage may rise as high as 5 or more volts, which is usually greater than the breakdown voltage. When this occurs, the aluminum cathode begins to form oxide by a hydration process which extracts oxygen from the water present in the electrolyte. The reaction produces hydrogen as a byproduct which in turn has the effect of creating an internal pressure within the capacitor, in various embodiments. Embodiments having internal pressure can demonstrate an undesirable mechanical bulge in the layers of the capacitor stack, or in the case. As such, the titanium-coated cathode described above serves as a corrective mechanism for hydrogen generation.

Various capacitor stack embodiments use separator layers 115A-N to electrically separate two layers. Separator layers 115A-N, in some embodiments, additionally serve as a carrier for an electrolyte. A separator layer 115A-N can include a single layer of kraft paper, or multiple layers of kraft paper, in various embodiments. In some embodiments, two layers of craft paper are used to isolate a first electrode from a second electrode. In some of these embodiments, each kraft paper layer is approximately 0.05 inches in thickness. In various embodiments, the electrolyte can be any electrolyte for an electrolytic capacitor, such as an ethylene-glycol base combined with polyphosphates, ammonium pentaborate, and/or an adipic acid solute.

Various embodiments of the present subject matter include one or more anode layers 114A-N. In various embodiments, anodes can include aluminum, tantalum, hafnium, niobium, titanium, zirconium, and combinations of these metals. Other compositions not listed herein expressly are also used as an anode.

In one embodiment, at least portions of a major surface of each anode is roughened and/or etched to increase its effective surface area. This option can increase the capacitive effect of the anode on a volumetric basis, in various embodiments. Various embodiments use tunnel-etched, core-etched, and/or perforated-core-etched structures. Various embodiments utilize other compositions. In various embodiments, at least one of anode layers 114A-N is a high formation voltage anode. In various embodiments, the anodes are medium and/or low formation variations. An anode layer 114A-N, in various embodiments, can include anode sublayers. In some embodiments, one anode layer is a multi-anode stack including three anode sublayers. In various embodiments, an anode layer can include one, two, three or more anode sublayers.

Depending on which process is used to construct the anode, various surfaces are coated with a dielectric. For example, in embodiments where the anode layers are punched from a sheet, which has previously been coated with dielectric, only the surfaces which have not been sheared in the punching process are coated with dielectric. Variously, if the dielectric is formed after punching, in various embodiments, all surfaces are coated. In some embodiments, anodes are punched from a larger sheet to minimize handling defects due to handling during the manufacturing process. For example, if a larger sheet is used as a starting material from which a number of anode layers are punched, machines or operators can grasp areas of the starting material which is not intended to form the final anode. Generally, in embodiments where the entire anode is not covered with dielectric, the anode is aged to restore the dielectric.

Various embodiments include a capacitor stack adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

In various embodiments, the stack is disposed in a case, and linked with other components, a state which affects some of these values. For example, in one packaged embodiment, including a case and terminals, the energy density available ranges from about 5.3 joules per cubic centimeter of capacitor stack volume to about 6.3 joules per cubic centimeter of capacitor stack volume. Some embodiments are adapted to deliver about 5.8 joules. In various embodiments, these ranges are available at a voltage of between about 410 volts to about 610 volts.

In various embodiments, a first capacitor stack configuration includes nine cathode layers, twenty separator layers, and twenty-eight anode layers. One way to form such a combination would be to stack eight elements including three anode layers and one element including two anode layers. The number of layers, and the number of elements, is selectable by a capacitor stack design and manufacturing process to achieve a desired capacitor power and thickness, in various embodiments.

In various embodiments, a second capacitor stack configuration includes nineteen cathode layers, forty separator layers, and fifty-eight anode layers. One way to form such a combination would be to stack eighteen first elements, with each first element including three anode layers, one cathode layer, and two separators, with a second element including two anode layers, one cathode layer, and with a third element including two separators, and two anode layers. The number of layers, and the number of elements, is selectable by a capacitor stack design and manufacturing process to achieve a desired capacitor power and thickness, in various embodiments. The configuration offered as an example should not be construed as limiting, as other configurations are possible depending on packaging and power needs of various applications.

In various embodiments of the present subject matter, a capacitor includes 8 anode layers. In additional embodiments, a capacitor includes 2 cathode layers. In some embodiments, a capacitor includes 20 anode layers. In some embodiments, a capacitor includes 7 cathode layers.

Various embodiments of the present subject matter define two capacitive capacitor subsets, including a first capacitor subset 102 and a second capacitor subset 104, by partitioning the capacitor stack 122 into a first partition $P_1$ and a second partition $P_2$. In some embodiments of the present subject matter, the two capacitor subsets are defined by two groups of interconnected anode layers. Interspersed among the two groups of interconnected anode layers are a group of interconnected cathode layers, in various embodiments. In various embodiments, the capacitor exhibits a first storage capacity in a first mode of operation, and a second storage capacity in a second mode of operation. The first mode of operation, and the second mode of operation, in various embodiments, are selected by opening and closing a switch 106. In some embodiments, the switch 106 is a pair of contacts which are connected mechanically. Some embodiments use solder or a jumper to interconnect the contacts. In additional embodiments, switch 106 is a semiconductor device which is controlled by software. In some embodiments, the software and the semiconductor are integrated into the capacitor 101, and the capacitor 101 is connected to electronics at terminals 111 and 112. In additional embodiments, the terminals 130 and 132, as well as the terminal 136, are connected to additional electronics. In these embodiments, the switch 106 is integrated with those additional electronics.

In additional embodiments, switch 106 is a semiconductor device which is controlled by software. In some embodiments, the software and the semiconductor are integrated into the capacitor 101, and the capacitor 101 is connected to electronics at terminals 111 and 112. In additional embodiments, the terminals 130 and 132, as well as the terminal 136, are connected to additional electronics. In these embodiments, the switch 106 is integrated with those additional electronics.

As discussed herein, the first partition and the second partition can be of different capacitances. In various embodiments, the first partition has a first capacitance value. In various embodiments, the partition has a second capacitance value. In some embodiments, the first and second capacitance values are equivalent. In additional embodiments, the first and second capacitance values are not equivalent. In some embodiments, one partition can store more energy than another partition. In some embodiments of the present subject matter, a first partition is sized to store approximately three times the energy of a second partition. As discussed herein, in implantable device embodiments, such a ratio of energy storage is useful to allow the capacitor partitions to be selected such that a first therapy energy level is available, and a second therapy energy level is available. Having a selectable therapy energy level allows capacitor designers and operators to adapt the implantable medical device to the requirements of multiple situations. Such adaptability, in various embodiments, can reduce surgery time and can improve the range of helpful treatments that are available to a patient.

In some examples within the present subject matter, a switchable capacitor is compatible with a range of patients exhibiting a range of implant site impedances. In various embodiments, a care provider implants a device into a patient. A sensor is used to establish impedance, in various embodiments. In some embodiments, the sensor is mounted to an implanted lead which extends from the device to a shock site, in various embodiments. A care provider, in various embodiments, measures impedance at the shock site. This impedance is patient specific and varies from patient to patient. In some embodiments, the impedance is between approximately 40 ohms and approximately 60 ohms.

A required pulse energy level is determined, in various embodiments. In some embodiments, a standard base level is used. In additional embodiments, a care provider induces fibrillation, and then shocks the patient to determine a conversion threshold. In various embodiments, the energy required for conversion is established as a base energy value, and a generic value is added to that base value. For example, if 5 joules are required for conversion, various embodiments add 10 joules and shock the patient with a 15 joule pulse during life saving therapies.

Capacitors within the present scope deliver a therapeutic pulse to a patient which is truncated. In various embodiments, a capacitor operates at a tilt level. A tilt level is the level at which a certain percentage of voltage in the capacitor has dissipated. For example, a tilt level of 60% represents a capacitor circuit which is designed to discharge until the voltage at the capacitor is 40% of what it was before the capacitor began to discharge. In various embodiments, switching is used to truncate capacitor dissipation. Embodiments within the present scope use a tilt voltage of from about 60% to about 80%. Some embodiments use a tilt voltage which is 66%.

The pulse duration is the time required to deliver energy. In various embodiments, the pulse duration is a function of tilt setting. The pulse duration is based, in part, on the impedance at the implant site. In various embodiments, design specifications limit care providers to wave forms of certain lengths, for example. If a device which is implanted in the patient demonstrates a pulse duration which is over a specified time limit, the device must be switched with a device which can deliver the required amount of energy without violating the specified time limit. As such, a care provider would have to explant a device, and replace it with a new device. In some embodiments, a design specification requires wave forms of a particular duration in a first region of the world in which a device is sold, and wave forms of a second duration in a second region of the world in which a device is sold. Embodiments of the present subject matter are suited to provide therapies in the United States and in Europe through the adjustment of switch 106. Such adjustability, in various embodiments, provides for an improved range of therapies care providers can administer.

A single capacitor stack including two capacitive capacitor subsets has several benefits. One benefit is that two capacitor subsets can be manufactured efficiently using manufacturing techniques used for capacitor stacks having a single capacitive capacitor subset. These benefits include the ability to weld along a single axis during the interconnection of multiple layers. These benefits additionally include the ability to quickly assemble a stack of fragile layers using pick and place technology. The benefits also include a reduction in process complexity. By eliminating one housing, the capacitor 101 offers reduced complexity. Along these lines, capacitor 101 can take the place of two capacitors in a parts inventory database. These are just some of the benefits the present design exhibits.

Figure 2:
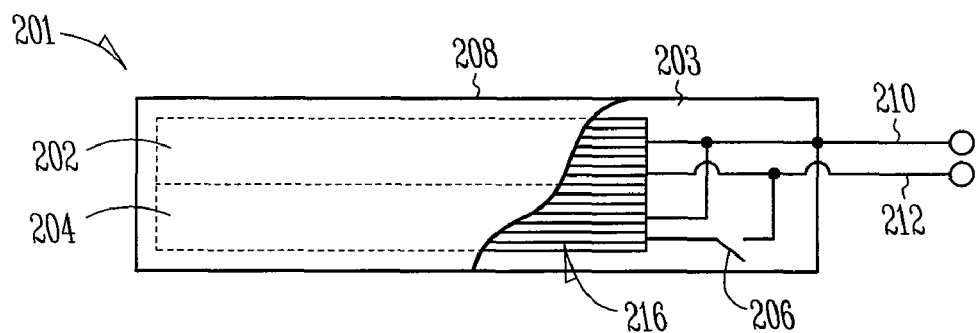
FIG. 2 shows a schematic side view of a power source including a capacitor subset stack, according to one embodiment of the present subject matter.

FIG. 2 shows a schematic side view of a power source including a capacitor subset stack, according to one embodiment of the present subject matter. In various embodiments, a power source 201 includes a first capacitor subset 202 and a second capacitor subset 204. Although the capacitor subset embodiments pictured are substantially flat and planar, other capacitor subset shapers are possible. The capacitor subset embodiments include a stack 216 of electrodes in various embodiments. Some embodiments include foil shaped electrodes. The capacitor subsets 202, 204 are disposed in a capacitor case 203.

In various embodiments, the capacitor case also houses a switch 206. Switch 206, in various embodiments, represents a pair of connection contacts inside the case 206 which are hardwired together during assembly. In additional embodiments, jumpers are used. Some embodiments include jumper accessible outside of a sealed implantable device. In other embodiments, high-current switch devices are used. In some embodiments, relays controlled by circuitry outside of case 206 are used. In some embodiments, switch 206 is a semiconductor device. In some embodiments, switch 206 is controlled wirelessly. Some of these embodiments use a wireless programmer to control the switch 206. In additional embodiments, switch 206 is controlled by computer software and hardware disposed in case 206. Some embodiments used feedthrough terminals 210 and 212 to program computer software and hardware which controls switch 206. This list is not exhaustive or exclusive of the present subject matter. Other switch embodiments not expressly recited herein additionally fall within the present scope.

Extending from the capacitor case and connected to the capacitor subsets 202, 204 are feedthrough terminals, in various embodiments. For example, some embodiments include an anodic feedthrough terminal 212. Additional embodiments include a cathodic feedthrough terminal 210. In some embodiments, the cathode terminal 210 is connected to the case 203, which is connected to a cathode of the capacitor. In some embodiments, the cathode terminal 210 is connected directly to the cathode of the capacitor.

It should be noted that embodiments discussed herein which include anodes and cathodes represent only a portion of the embodiments within the scope of the present subject matter. In additional embodiments, electrodes which are disclosed as being anodic are cathodic. Similarly, in additional embodiments, electrodes which are disclosed as being cathodic are anodic.

Figure 3A:
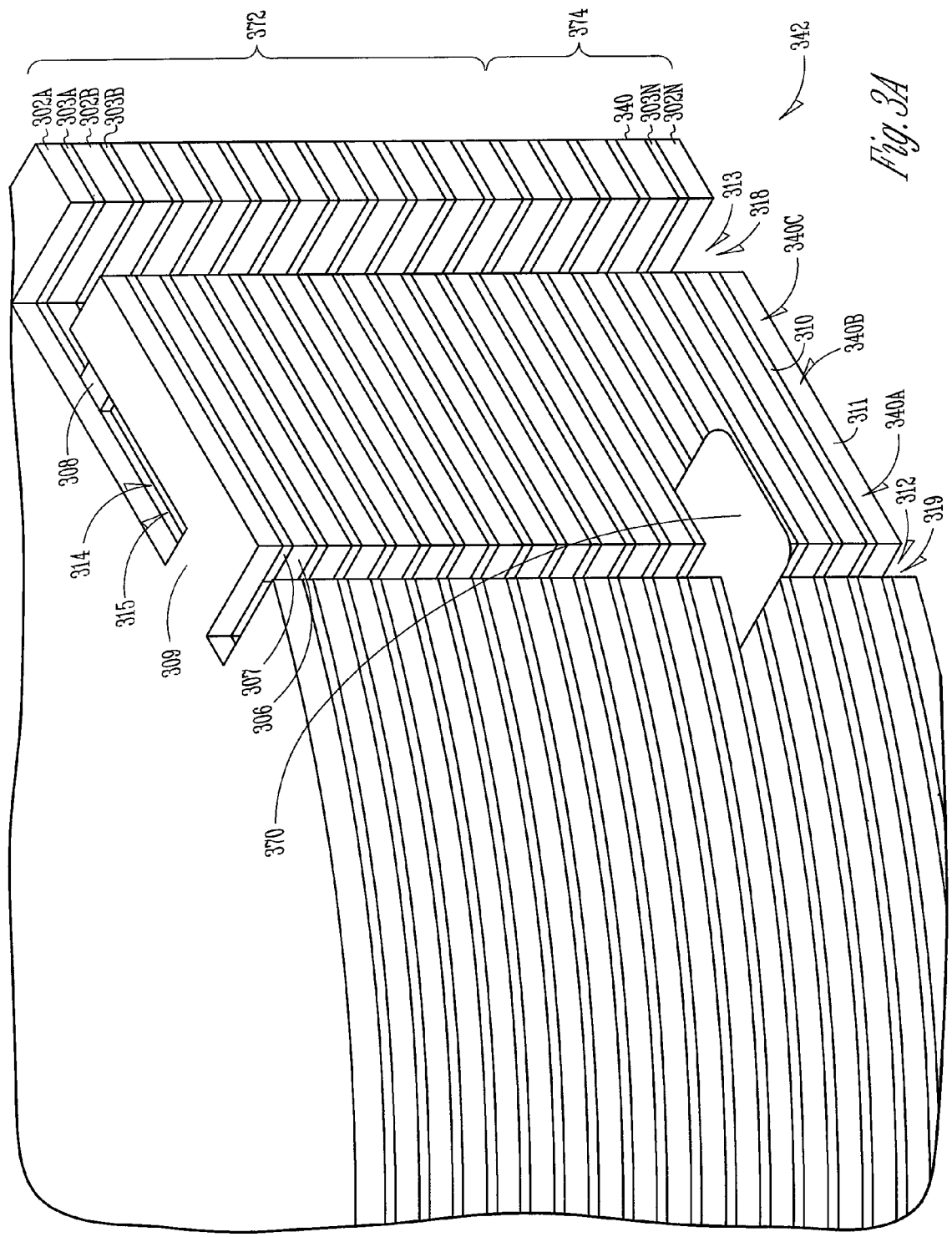
FIG. 3A shows a schematic side view of a power source including a capacitor subset stack, according to one embodiment of the present subject matter.

FIG. 3A is a partial perspective view of a capacitor stack of one or more anodes and cathodes, according to one embodiment of the present subject matter. Various embodiments include a stack 342 of one or more alternating anode layers 302 and cathode layers 303. As shown in FIG. 3A, connection members 306 and 307 are overlaying and underlying each other. In various embodiments connection members 306 and 307 have some commonly positioned portions relative to each other and some portions which are exclusively positioned relative to each other. The pictured embodiment is one embodiment in which an anode connection member and a cathode connection member are aligned with one another along the direction of stacking.

For instance, proximal sections 309 of anode layers 302 are exclusively positioned or located. This means that at least a portion of proximal sections 309 do not overlay or underlay a portion of cathode 303. Likewise, proximal sections 308 of cathode 303 are exclusive portions and include at least a portion not overlaying or underlaying a portion of anode layers 302. Conversely, distal sections 311 and 310 are commonly positioned and each includes at least a portion overlaying or underlaying each another. Cut-out portions 315 and 314 are also commonly positioned. Cut-out 319 is commonly positioned with cut-out 312 while cut-out 313 is commonly positioned with cut-out 318.

In various stacked embodiments the edges of distal sections 311 and 310 form a surface 340. In some of these embodiments, surface 340 can generally be described as including a first portion 340A which fronts the proximal sections 309 of anode layers 302, a second portion 340B which fronts common cut-portions 315 and 314, and third portion 340C which fronts the proximal sections 308 of cathode layers 303.

In various embodiments, distal sections 311 and 310 of anode connection member 307 and cathode connection member 306 are fully overlaying one another. Fully overlaying means that there are generally no gaps along surface 340 of stack 342 when the anodes and cathodes are stacked. The fully overlayed structure of stack 342 provides a complete surface 340 which provides for ease of edge-welding or otherwise connecting connection members 307 and 306 together. Other embodiments leave one or more gaps in surface 340 when the anodes and cathodes are stacked. For instance, in some embodiments, one or more of distal sections 311 or 310 may not reach all the way across front surface 340.

After being stacked as discussed above, at least portions of connection members 307 and 306 are connected to each other. For instance, in one embodiment, portions of distal sections 311 and 310 are connected to each other. In one embodiment, distal sections 311 and 310 are edge-welded at least partially along surface 340. In one embodiment, distal sections 311 and 310 are only connected along portion 340A and 340C of surface 340. In one embodiment, distal sections 311 and 310 are soldered along surface 340. In some embodiments, portions of distal sections 310 and 311 are staked, swaged, laser-welded, and/or connected by an electrically conductive adhesive. In other embodiments, portions of proximal sections 309 are connected to each other and/or portions of proximal sections 308 are connected to each other. In various embodiments, insulator 370 assists in electrically isolating a first edge weld and a second edge weld. In some embodiments, the insulator is a piece of separator paper. Other embodiments, the insulator is another insulative material. In embodiments, the first edge weld defines a first capacitor 372, and a second edge weld defines a second capacitor 374. Additionally, some embodiments use a single edge weld to interconnect all the cathode layers 303.

After being connected, portions of connection members 307 and 306 are removed or separated so that proximal sections 309 and 308 are electrically isolated from each other. In some embodiments, a single edge weld interconnects anode layers 302 of capacitor subset 372, and then the joined anode layers 302 are excised into two or more capacitor subsets. In one embodiment, a laser cut divides interconnected anode layers 302 into two or more capacitor subsets. In alternate embodiments, the anode layers 302 are connected, and the cathode layers 303 are excised into two or more capacitor subsets.

Figure 3B:
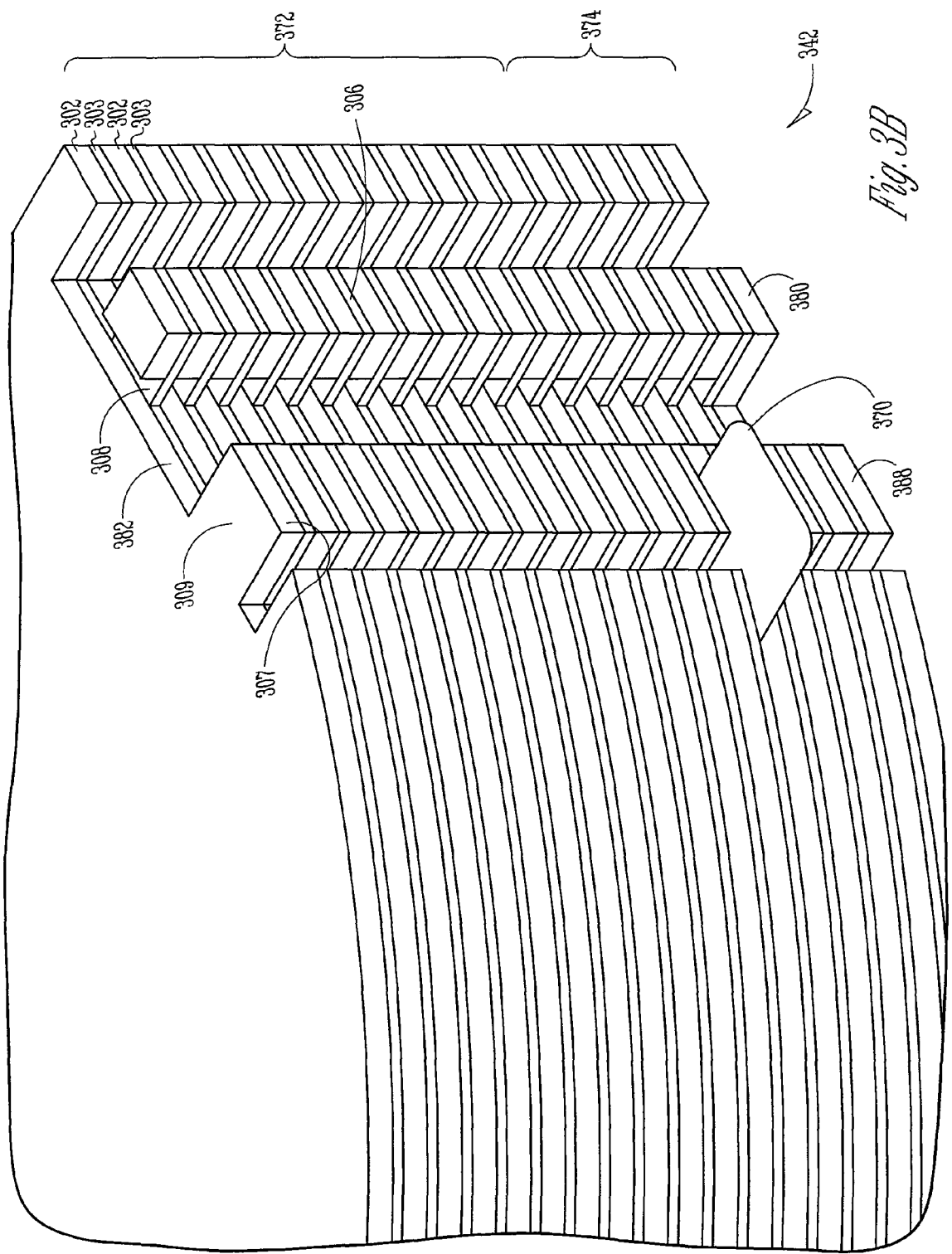
FIG. 3B is a perspective view of the stack of FIG. 3A after the stack has been processed according to one embodiment of the present subject matter.

FIG. 3B is a perspective view of the stack of FIG. 3A after the stack has been processed according to one embodiment of the present subject matter. FIG. 3B shows stack 342 after portions of distal sections 311 and 310 have been removed from the stack, forming a separation 382 between anode connection members 307, which together comprise anode connection section 388, and cathode connection members 306, which together comprise cathode connection section 380. Separation 382 in the present embodiment electrically isolates section 388 from section 380. Proximal sections 308 are still coupled to each other as are proximal sections 309. In some embodiments, separation 382 is a thin slice. In some embodiments, separation 382 is a wide cut-out. In some embodiments, an electrically insulative material is inserted in separation 382. In various embodiments, separation 382 is formed by laser cutting, punching, and/or tool or machine cutting. Separator 370 isolates first capacitor subset 372 from second capacitor subset 374.

Figure 4A:
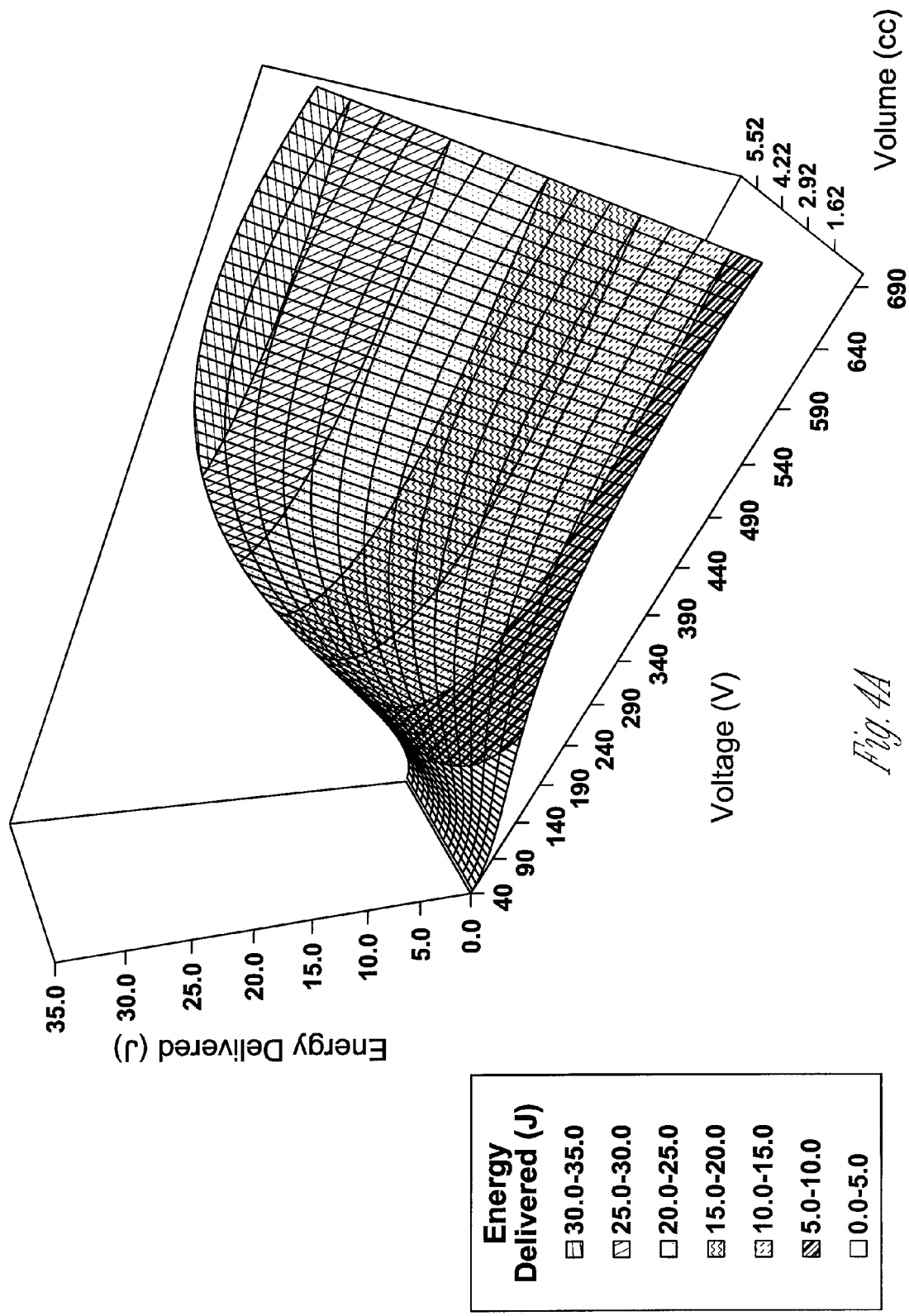
FIG. 4A illustrates a graph representing characteristics of a capacitor, according to various embodiments of the present subject matter.
Figure 4B:
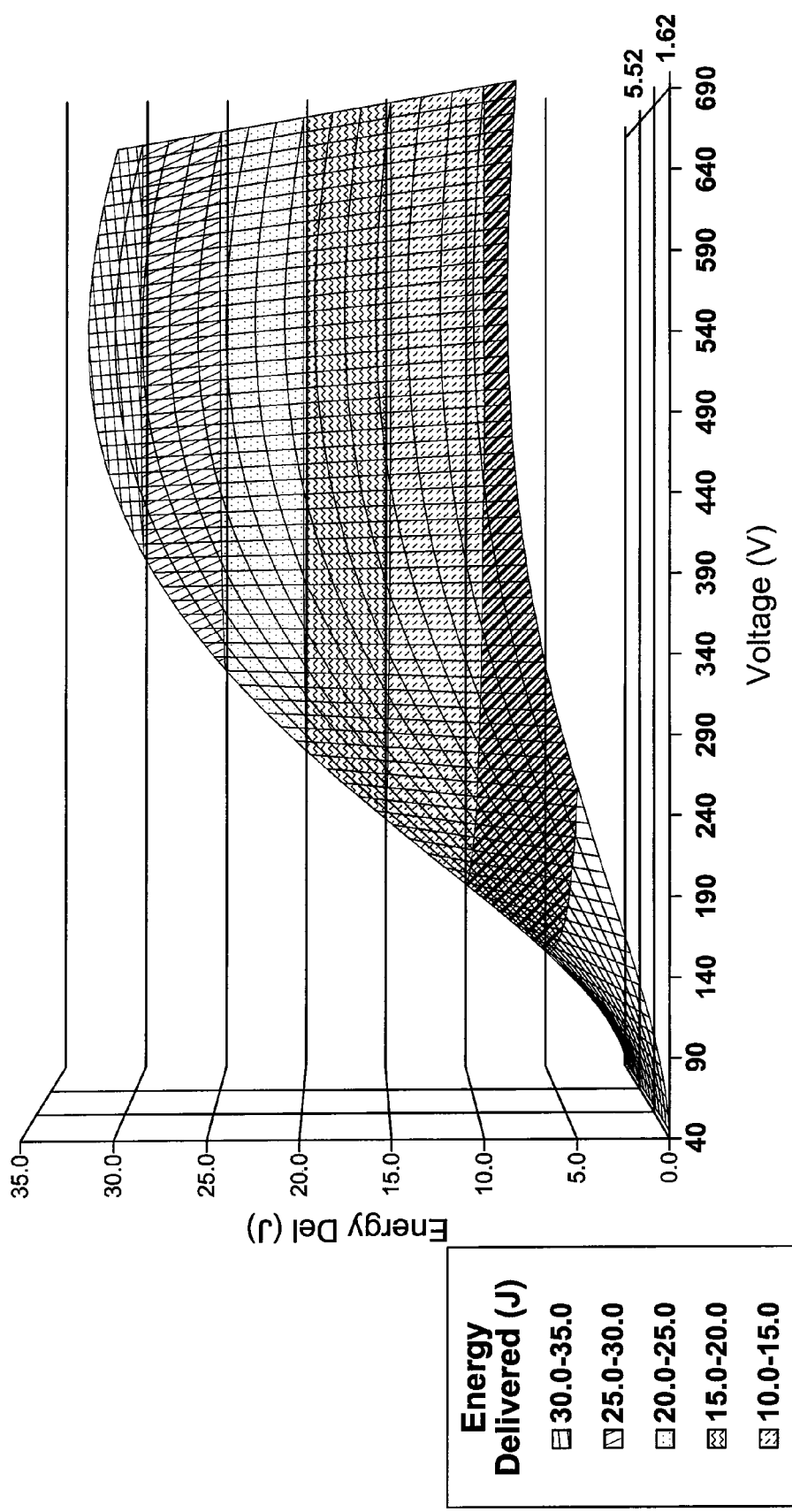
FIG. 4B illustrates a graph representing characteristics of a capacitor, according to various embodiments of the present subject matter.
Figure 4C:
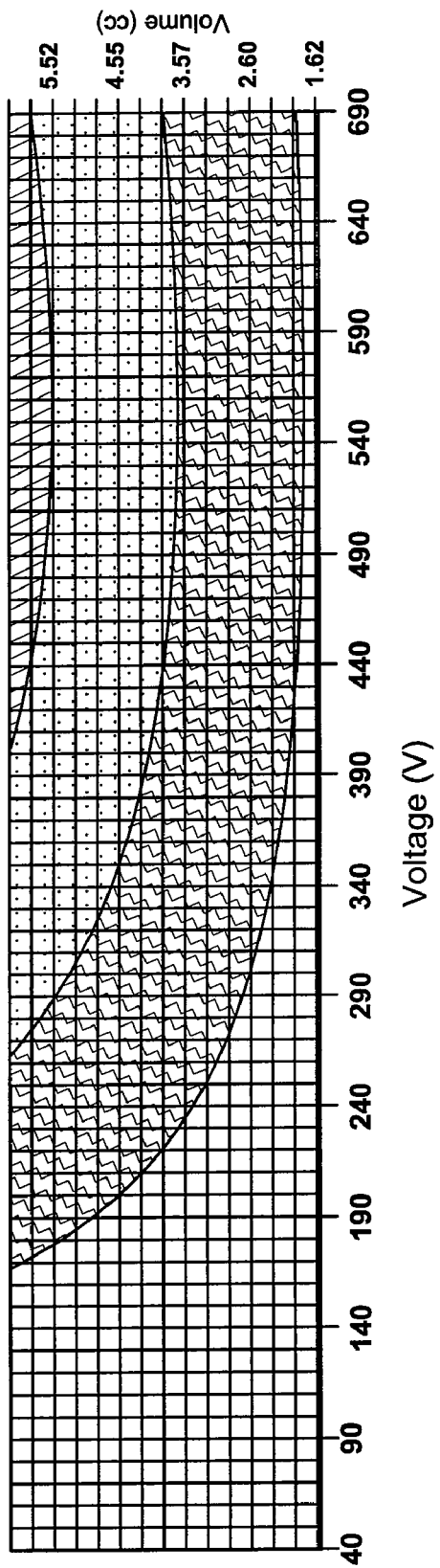
FIG. 4C illustrates a graph representing characteristics of a capacitor, according to various embodiments of the present subject matter.

FIGS. 4A-4C illustrate a graph representing characteristics of various embodiments of a capacitor, according to the present subject matter. The teachings of the present subject matter include a process for producing a capacitor which exhibits the traits illustrated by the graph. Among the various properties demonstrated by the graph are practical limitations tied to various aspects of capacitor design. Overall, the graph is useful to illustrate aspects which aid in selection and development of improved capacitors.

The graph includes a three dimensional curve representing energy delivered in joules, voltage in volts, and volume in cubic centimeters. Depending on which aspects of the graph are analyzed, various trends are apparent.

For example, FIG. 4A demonstrates embodiments in which a capacitor delivers improved energy in the range of about 465V to about 565V. The graph illustrates both the relationship between voltage and energy delivered, and volume and energy delivered. From reading and understanding the graph, it is apparent that higher voltages enable higher energy delivered, and that a higher capacitor volume enables higher energy delivered. The particular shape of the curves, and the energy delivered, are, in part, functions of the surface shape of the capacitor. For example, embodiments including capacitors with increased surface area due to etching, which have a dielectric formed on the surface area without substantial reduction in the surface area, provide more energy per volumetric unit. Additionally, embodiments which have increased dielectric thickness enable higher voltages, which also result in higher available energy levels. The present subject matter reveals varying preferential ranges considering these criteria.

For example, one embodiment of the present subject matter is adapted to deliver an electrical pulse at a voltage of between approximately 490 volts and approximately 540 volts. One embodiment is adapted to deliver an electrical pulse at approximately 515 volts. And additional embodiment is adapted to deliver an electrical pulse at approximately 550 volts. In some embodiments, a compromise is necessary to achieve the preferred performance. For example, in embodiments where approximately 515 volts is chosen as the operating voltage, an electrolyte which is unable to withstand higher voltages is used. In varying embodiments, an electrolyte which is unable to operate at the peak of the voltages curve evident in the graph is chosen because of technology limitations and cost limitations. However, it is to be understood that the present subject matter encompasses embodiments which operate at the voltages demonstrated by the graph, and the examples included in these teachings are provided solely for illustration, and are not exhaustive or exclusive.

Additionally, the present subject matter includes embodiment adapted to deliver from about 5.3 joules per cubic centimeter of capacitor stack volume to about 6.3 joules per cubic centimeter of capacitor stack volume. Also, the present subject matter teaches embodiments adapted to deliver from about 5.5 joules per cubic centimeter of capacitor stack volume to about 6.1 joules per cubic centimeter of capacitor stack volume. One embodiment is adapted to deliver about 5.8 joules per cubic centimeter of capacitor stack.

FIG. 4B shows a top view of a graph representing various properties of one capacitor embodiment of the present subject matter. The graph illustrates, in part, the relationship between voltage and energy delivered.

FIG. 4C includes a view of the graph which demonstrates the relationship, in part, between volume and energy delivered. In varying embodiments, the graph teaches that volumetric energy density, measured in joules per volt, increases when volume is minimized for a required energy delivered.

Thus, by reading and understanding the information provided by the graph, it is possible to produce a capacitor with an improved packaging density, including, in part, improved volumetric energy density.

Figure 5:
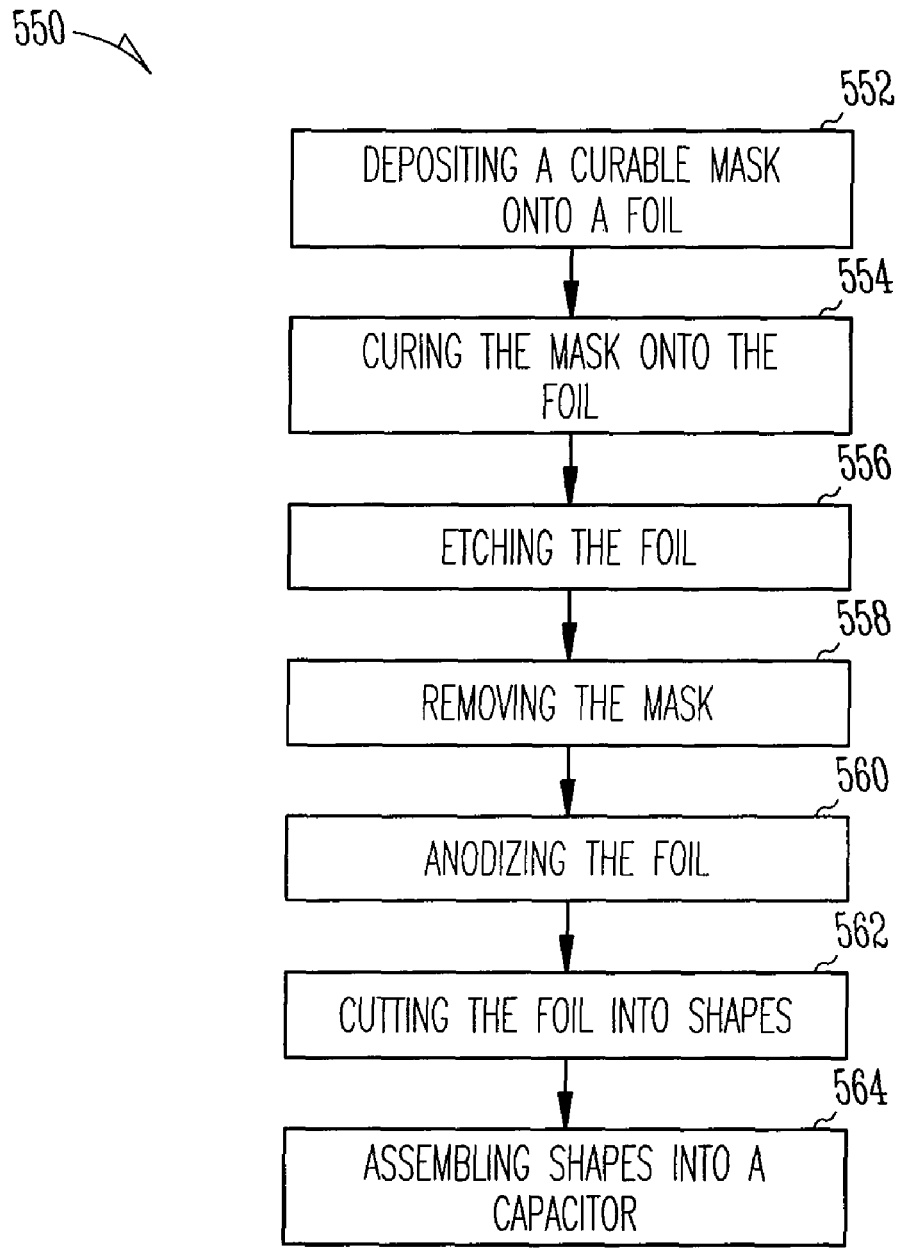
FIG. 5 illustrates a process for manufacturing a foil with a partially etched area, according to one embodiment of the present subject matter.

FIG. 5 shows a process for making a foil with a partially etched area, according to various embodiments of the present subject matter. In varying embodiments, the process includes depositing a curable mask onto a foil 552. For example, in one embodiment, the mask is deposited on a foil using a computer controlled mask dispensing system. In one example, ink is deposited using an ink-jet process.

Various embodiments cure the mask onto the foil 554. Examples of curable mask include ink, and photoresist. In varying embodiments, the curable mask is cured to the foil. For example, in one embodiment, ink is deposited on the foil, and then is baked to the foil in an oven. Baking, in some embodiments, exposes the curable mask to radiant heat energy, which can increase hardness or the curable mask, and which also can decrease the time needed for curing. In varying embodiments, the oven is adapted to cure the curable mask without affecting the foil otherwise.

In varying embodiments, the foil is etched 556, and the mask protects the foil from the etchant. In various embodiments, etching includes core-etching the foil, tunnel-etching the foil, perforating the foil and combinations and permutations of these techniques. In some embodiments, perforations are formed using lasers, chemical etchants, or mechanical dies, for example. Some embodiments tunnel-etch the foil, other embodiments provide other known methods of providing a porous or etched foil. In some embodiments, a porous anode structure is constructed using other roughening or etching techniques.

Varying examples of the process then remove the mask 558. Removing the mask, in one embodiment, includes submerging the foil with mask in a solution adapted to dissolve the mask.

Some embodiments anodize the foil 560 to form a dielectric. In one embodiment, forming a dielectric layer comprises forming a layer of $Al_2O_3$ having a thickness in the range of 573 nm to 1200 nm on the anode foil (assuming a dielectric growth rate of 1.3-1.5 nm/v). In one embodiment, the dielectric layer is formed on the anode before the capacitor stack is constructed.

In one embodiment, forming the dielectric layer includes applying a current through the anode and raising the voltage to the rated formation voltage. In one embodiment, the formation voltage is 441 volts. In other embodiments, the forming voltage is 450, 500, 550, 600, and 600-800 volts, and other voltages ranging from approximately 441 to approximately 800 volts or greater. The current causes a dielectric $Al_2O_3$ to form on the surface of the foil. Once the formation voltage is reached, the capacitor is held at that voltage until a leakage current stabilizes at a predetermined level. By monitoring the rising voltage and/or the leakage current, the oxide formation can be estimated. Once the preset voltage is reached, it plateaus, in which case a current drop ensues in order to balance the increasing resistance of oxide film growth. The process is complete when the current drops to a pre-specified value. Some embodiments combine etching and dielectric forming so that the etching and dielectric forming are done simultaneously.

In one embodiment, method 550 results in an aluminum anode foil having a formation voltage between approximately 441 volts and approximately 600 volts. In various embodiment, this includes a foil having a formation voltage of approximately 441, approximately 450, approximately 500, approximately 550, approximately 600, and approximately 600 volts to approximately 800 volts or greater. Varying embodiments form a dielectric at approximately 600 volts to approximately 760 volts. In one embodiment, a dielectric thickness sufficient to withstand between about 653 volts and about 720 volts develops during formation. Other embodiments withstand from about 667 volts to about 707 volts during formation. One example is able to withstand about 687 volts during formation.

Varied processes can be utilized to produce the aluminum foil of the present subject matter. For example, one process includes forming a hydrous oxide layer on an aluminum foil by immersing the foil in boiling deionized water. The aluminum foil is also subjected to electrochemical anodization in a bath containing an anodizing electrolyte composed of an aqueous solution of boric acid, a phosphate, and a reagent. Additionally, the anodizing electrolyte contains a phosphate. In various embodiments, the anodizing electrolyte is at a pH of approximately 4.0 to approximately 6.0. In some examples, the foil is passed through a bath containing a borax solution. Borax, in various embodiments, includes a hydrated sodium borate, $Na_2B_4O_7.10H_2O$, and is an ore of boron.

In varying embodiments, the foil is reanodized in the boric acid-phosphate electrolyte previously discussed. In various embodiments of the present subject matter, the process produces a stabilized foil suitable for oxide formation of up to approximately 760 volts.

In various embodiments, the anodizing electrolyte contains about 10 grams per liter to about 120 grams per liter of boric acid and approximately 2 to approximately 50 parts per million phosphate, preferably as phosphoric acid, and sufficient alkaline reagent to lower the resistivity to within approximately 1500 ohm-cm to approximately 3600 ohm-cm and increase the pH from about 4.0 to about 6.0 for best anodization efficiency and foil quality.

In some embodiments, the borax bath contains 0.001 to 0.05 moles/liter of borax. Because the anodizing electrolyte is acidic, in various embodiments, the borax bath is buffered with sodium carbonate to prevent lowering of the pH by dragout of the acidic electrolyte. Additionally, in various embodiments, the borax bath is buffered to lower its resistivity. In one example, the pH of the bath is from about 8.5 to about 9.5, and the temperature is at least approximately 80 degrees Celsius. In varying embodiments, the sodium concentration is approximately 0.005 to approximately 0.05M, preferably about 0.02 M. It should be noted that concentrations of less than approximately 0.005M are too dilute to control properly, and concentrations above approximately 0.05M increase the pH, resulting in a more reactive solution which degrades barrier layer oxide quality.

In varying embodiments of the present subject matter, the presence of at least approximately 2 parts per million phosphate in the acidic anodizing electrolyte is critical. For example, this presence initiates stabilization of the foil so that solely hydrous oxide dissolves in the alkaline borax bath, without damage to the barrier layer dielectric oxide. In varying embodiments, this lowers ESR (equivalent series resistance) of the anodized foil.

Additionally, in various embodiments, when the foil is reanodized following the alkaline borax bath, the foil surface is alkaline and reacts electrochemically with the phosphate, which, in various embodiments, results in the incorporation of phosphate into the dielectric oxide. In varying examples, the alkaline foil surface includes an alkaline metal aluminate, and in one embodiment includes a sodium aluminate. It should be noted that the amount of allowable phosphate in the anodizing electrolyte, in various embodiments, is inversely proportional to the voltage at which the foil is being anodized. For example, in one embodiment, using greater than approximately 24 parts per million results in failure during oxide formation at around 650 volts. In embodiments where approximately 50 parts per million of phosphate is exceeded, the electrolyte scintillates at the foil interface, resulting in damaged, unstable foil. One benefit of the present subject matter is that an electrode is produced which can tolerate a high formation voltage without scintillation at the boundary layer of the foil. It should be noted that anodization temperature should be maintained from about 85 degrees Celsius to about 95 degrees Celsius, as variance outside of these values results in a barrier layer oxide of lower quality, and foil corrosion.

It should be noted that these teachings should not be understood to be exhaustive or exclusive, and other methods of forming a dielectric on a foil are within the scope of the present subject matter. Additionally, it should be noted that other examples anodize the foil while the mask is in place.

In addition, varying embodiments cut the anodized foil into shapes 562, and in some examples, the foil shapes are then assembled into a capacitor 564.

According to various embodiments, an apparatus is disclosed for providing a selective capacitance. The apparatus includes multiple capacitive elements and a switching circuit connected between the capacitive elements. According to various embodiments, the switching circuit is adapted to programmably connect a plurality of the capacitive elements to provide a desired defibrillation capacitance. The switching circuit is adapted to programmably connect a plurality of the capacitive elements to selectively charge connected elements for use in a defibrillator, according to various embodiments. The capacitive elements are housed in an implantable medical device, according to various embodiments.

In varying embodiments, the switching circuit is housed with the capacitive elements. In other embodiments, the switching circuit is housed separate from the capacitive elements. The switching circuit is housed adjacent to the capacitive elements, in further embodiments. The switching circuit can be accessible from outside the implantable medical device via wireless communication. Examples of wireless communication include inductive telemetry and radio frequency (RF) telemetry. According to various embodiments, the switching circuit is accessible from outside a human body in which the device is implanted via wireless communication. The apparatus may further include a flyback capacitor charger adapted to connect in parallel with the capacitive elements in an embodiment. According to one embodiment, the capacitive elements include a first and second capacitor in a stack. As discussed, the first and second capacitors can include a plurality of substantially planar electrodes, in varying embodiments.

Another embodiment of the apparatus includes a first and second capacitor in a stack, the first and second capacitors including a plurality of substantially planar electrodes. The apparatus embodiment also includes a switching circuit connected between the first and second capacitors. The switching circuit has at least two states, and is adapted to provide a first defibrillation capacitance in a first state and a second defibrillation capacitance in a second state, according to various embodiments. According to varying embodiments, the stack includes a common cathode which is shared by the first and second capacitor. The first defibrillation capacitance is equal to a capacitance of the first capacitor and the second defibrillation capacitance is equal to the sum of the capacitance of the first capacitor and a capacitance of the second capacitor, according to various embodiments.

Figure 6:
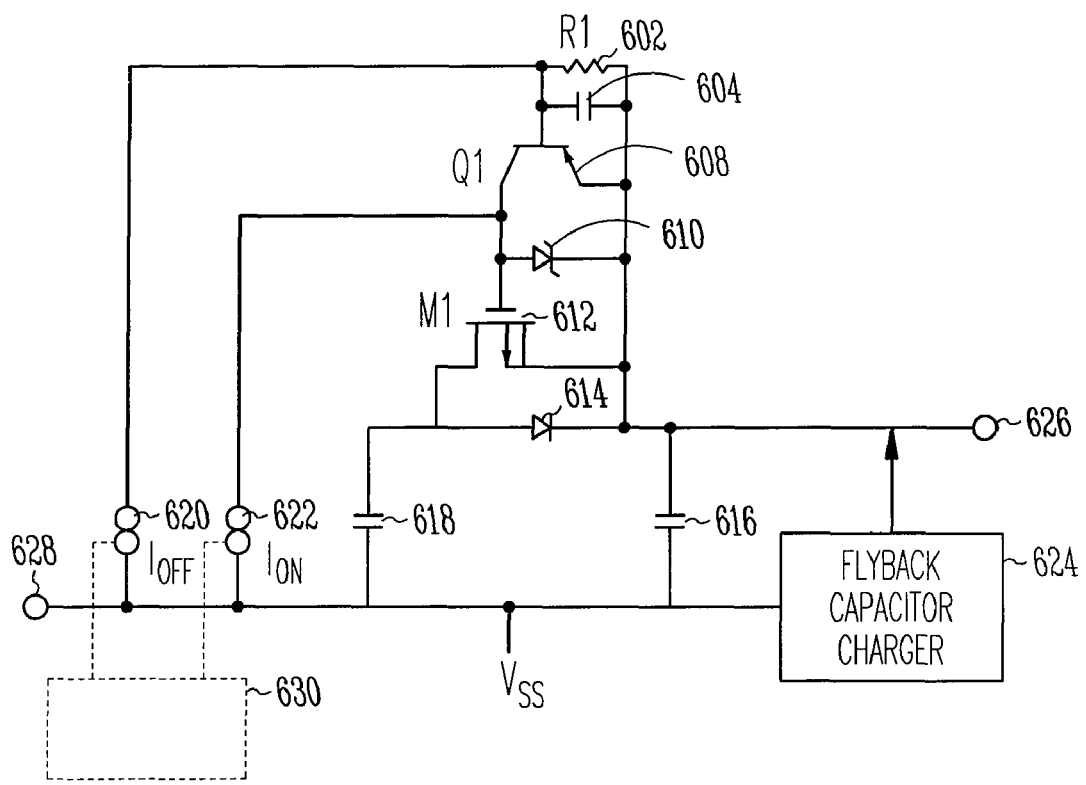
FIG. 6 shows a circuit for charging and discharging one or more capacitor subsets of a multi-capacitor subset capacitor stack, according to one embodiment of the present subject matter.

FIG. 6 shows a circuit for charging and discharging one or more capacitor subsets of a multi-capacitor subset capacitor stack, according to one embodiment of the present subject matter. The circuit apparatus includes a first capacitor 616 and second capacitor 618 in a stack, the first and second capacitors including a plurality of substantially planar electrodes. The apparatus embodiment also includes a switching circuit connected between the first and second capacitors. In this embodiment, the switching circuit includes a field effect transistor (FET, 612) adapted to have a source connected to the first capacitor and a drain connected to the second capacitor, a bipolar junction transistor (BJT, 608) adapted to have an emitter connected to the source of the FET and a collector connected to a gate of the FET, a first current source 622 connected to the collector of the BJT, and a second current source 620 connected to a base of the BJT. According to various embodiments, activating the first current source 622 turns the FET on, connecting the first and second capacitors, and activating the second current source 620 turns the FET off, isolating the first and second capacitors.

The FET 612 includes a 600 volt p-channel MOSFET, according to various embodiments. Other sizes and types of FETs may be used within the scope of this disclosure. The FET can have a relatively high 'on' resistance (such as 20 ohms, in an embodiment) because the FET conducts charging current. The BJT 608 includes a small, low voltage pnp bipolar junction transistor, such as part number 2N2907, according to an embodiment. Other sizes and types of BJTs may be used within the scope of this disclosure.

According to various embodiments, the stack includes a common cathode which is shared by the first and second capacitor. The apparatus also includes a diode 614 adapted to connect the source of the FET to the drain of the FET. The diode 614 is adapted to conduct pulse current during discharge of the second capacitor, and according to various embodiments is adapted to have 600 volt capacity. Other sizes and types of diodes may be used within the scope of this disclosure. According to various embodiments, the apparatus also includes a second diode 610 adapted to connect the collector of the BJT to the emitter of the BJT. The second diode 610 may include a 10 volt zener diode. Other sizes and types of second diodes may be used within the scope of this disclosure. According to various embodiments, the apparatus includes a flyback capacitor charger 624 adapted to connect in parallel with the first capacitor.

A resistor 602 is adapted to connect the base of the BJT to the emitter of the BJT, according to various embodiments. The resistance value of the resistor 602 is selected to prevent the BJT from turning on due to off-state leakage current from the second current source. Thus the resistance value of resistor 602 should be less than or equal to the voltage drop across the base-emitter junction divided by the leakage current. In various embodiments, the resistor 602 is connected in parallel with a capacitor 604, which has a value of around 10 nF according to an embodiment. Node 628 is adapted to connect to the supply voltage (Vss) and node 626 is adapted to connect to a device output, such as a defibrillator bridge, according to various embodiments.

In the depicted embodiment, both the first 616 and second 618 capacitors are connected to the output node 626 when the first current source 622 is activated during capacitor charging. In this embodiment, only the first capacitor is connected to the output node 626 when the second current source 620 is activated while high voltage is present on the first capacitor 616, which turns on BJT 608 and removes gate drive from FET 612, turning it off.

According to various embodiments the first and second capacitors are housed in an implantable medical device. The switching circuit may be housed with, adjacent to, or separate from the first and second capacitors in various embodiments. The switching circuit may be accessible from outside the implantable medical device using a controller 630, according to an embodiment. In one embodiment, the switching circuit is accessible from outside a human body in which the device is implanted.

Another embodiment of the apparatus includes a first capacitor subset of a multi-capacitor subset capacitor stack, a second capacitor subset of a multi-capacitor subset capacitor stack and a switching circuit connected between the first and second capacitor subsets, the switching circuit adapted to charge and discharge the capacitor subsets. In this embodiment, the switching circuit includes a high voltage field effect transistor (FET) connected between the first and second capacitors, a low voltage bipolar junction transistor (BJT) connected between a gate and source of the FET, a first current source connected to the gate of the FET, and a second current source connected to a base of the BJT. According to various embodiments, activating the first current source turns the FET on, connecting the first and second capacitor subsets, and activating the second current source turns the FET off, isolating the first and second capacitor subsets.

According to various embodiments, the first capacitor subset is adapted to store approximately three times the energy of the second capacitor subset. According to one embodiment, the first capacitor subset stores around 31 Joules. The second capacitor subset stores around 10 Joules, in an embodiment.

One aspect of this disclosure relates to a method for making an apparatus with a variable defibrillation capacitance. According to an embodiment of the method, a first and second capacitor are formed in a stack, the first and second capacitors including a plurality of substantially planar electrodes, and a switching circuit is connected between the first and second capacitors. The switching circuit includes a first and second state, and selecting the first state selects the first and second capacitor to provide a defibrillation capacitance. Selecting the second state selects the first capacitor to provide a defibrillation capacitance, according to various embodiments. According to an embodiment, forming the first capacitor includes forming the first capacitor to store around 31 Joules. Forming the second capacitor includes forming the second capacitor to store around 10 Joules, according to one embodiment.

One aspect of this disclosure relates to a method for making an apparatus for charging partitioned capacitors. According to an embodiment of the method, a first and second capacitor are formed in a stack, the first and second capacitors including a plurality of substantially planar electrodes, and a switching circuit is connected between the first and second capacitors. The switching circuit includes a field effect transistor (FET) connected between the first and second capacitors, a bipolar junction transistor (BJT) connected between a gate and source of the FET, a first current source connected to the gate of the FET, and a second current source connected to a base of the BJT. Selectively activating the first current source turns the FET on, connecting the first and second capacitors, and selectively activating the second current source turns the FET off, isolating the first and second capacitors according to various embodiments.

According to an embodiment, connecting a FET includes connecting a p-channel MOSFET and connecting a BJT includes connecting a PNP transistor. In various embodiments, forming a first and second capacitor in a stack includes stacking into a stack a plurality of substantially planar capacitor electrodes, the stack include at least a first and second anode layer and a plurality of cathode layers, positioning the stack in the case, connecting the first anode layer to a first feedthrough disposed through the case, connecting the second anode layer to a second feedthrough disposed through the case, and connecting the plurality of cathode layers to the case. In various embodiments, connecting a switching circuit between the first and second capacitors includes connecting the first feedthrough, the second feedthrough, and the case to the switching circuit.

The present subject matter includes embodiments which operate in various ways. Some applications in which the present subject matter is used include a design specification which requires that a defibrillator not deliver a therapeutic shock pulse which lasts longer than a pulse duration limit when operating at a specified tilt. The pulse duration limit in various embodiments is 20 milliseconds, and other times are used as well. Designing a pulse which does not exceed a pulse duration limit, but which delivers a required amount of energy, is straightforward if the impedance of the target is known. Unfortunately, the impedance of the target is not always known. In embodiments in which a device is implanted in a patient, target impedance is not known because of anatomical variations. As such, impedance of a target is not known until the therapeutic device is implanted. Embodiments using a device with an active housing additionally demonstrate this phenomenon. As such, care providers often must select a capacitor for an application after a device has been implanted, and site impedance has been measured. This can prolong surgery, because an initial impedance which is incorrect can require device removal and replacement during surgery.

To address the problem of unknown impedance, the present subject matter includes embodiments which allow for selecting two or more different capacitances without device removal. By controlling the state of a switch, care providers can select between the first capacitance and a second capacitance. Varying capacitances are able to deliver required energy levels at different times. Embodiments within the scope of the present subject matter can switch two capacitors into a parallel relationship so that the operating voltage is the same, while capacitance and energy are increased. Pulse duration is adjusted accordingly. Various embodiments include more than two capacitors.

Figure 7:
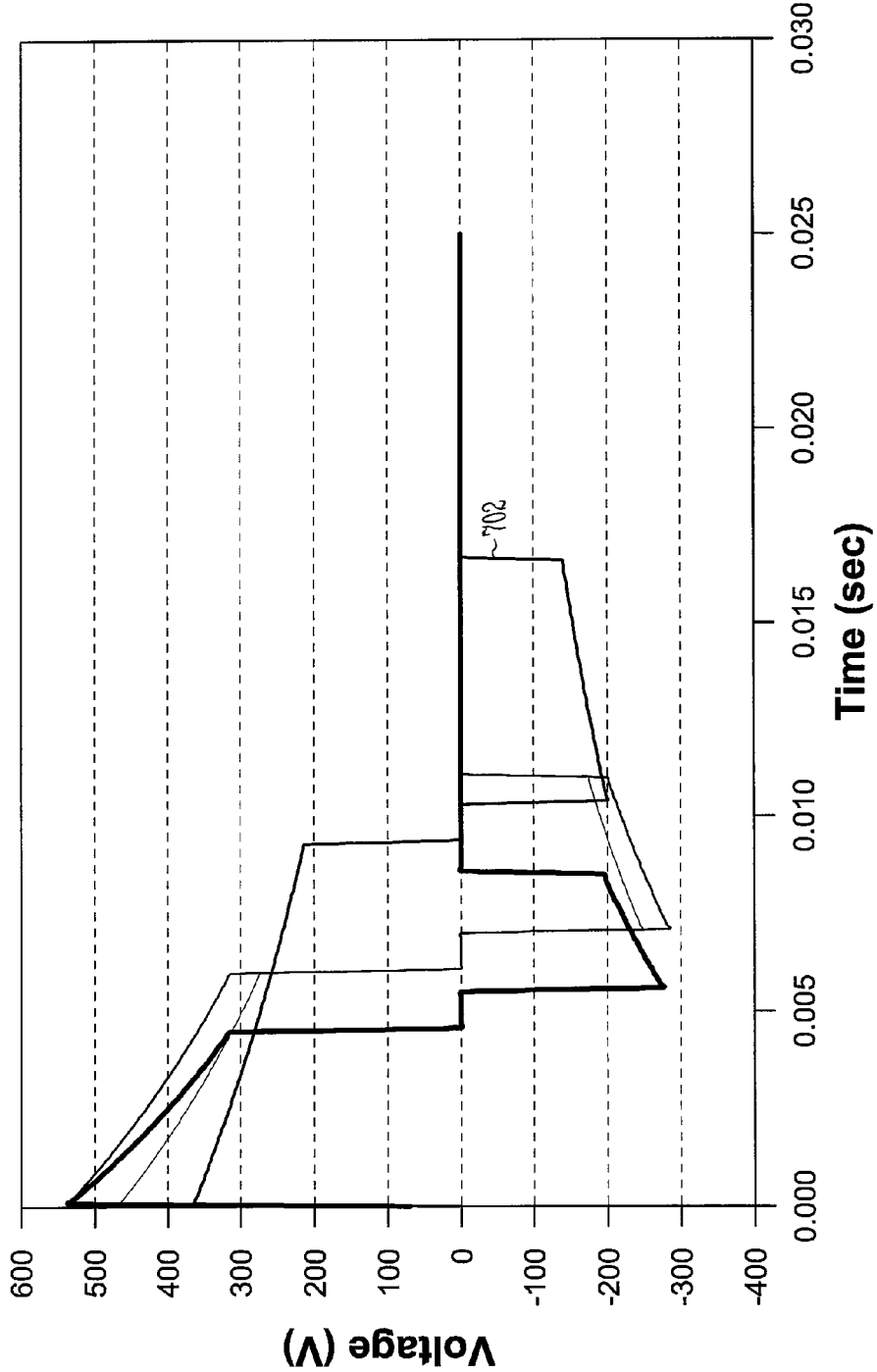
FIG. 7 shows various capacitor wave forms based on a 40 ohm load, according to various embodiments of the present subject matter.
Figure 8:
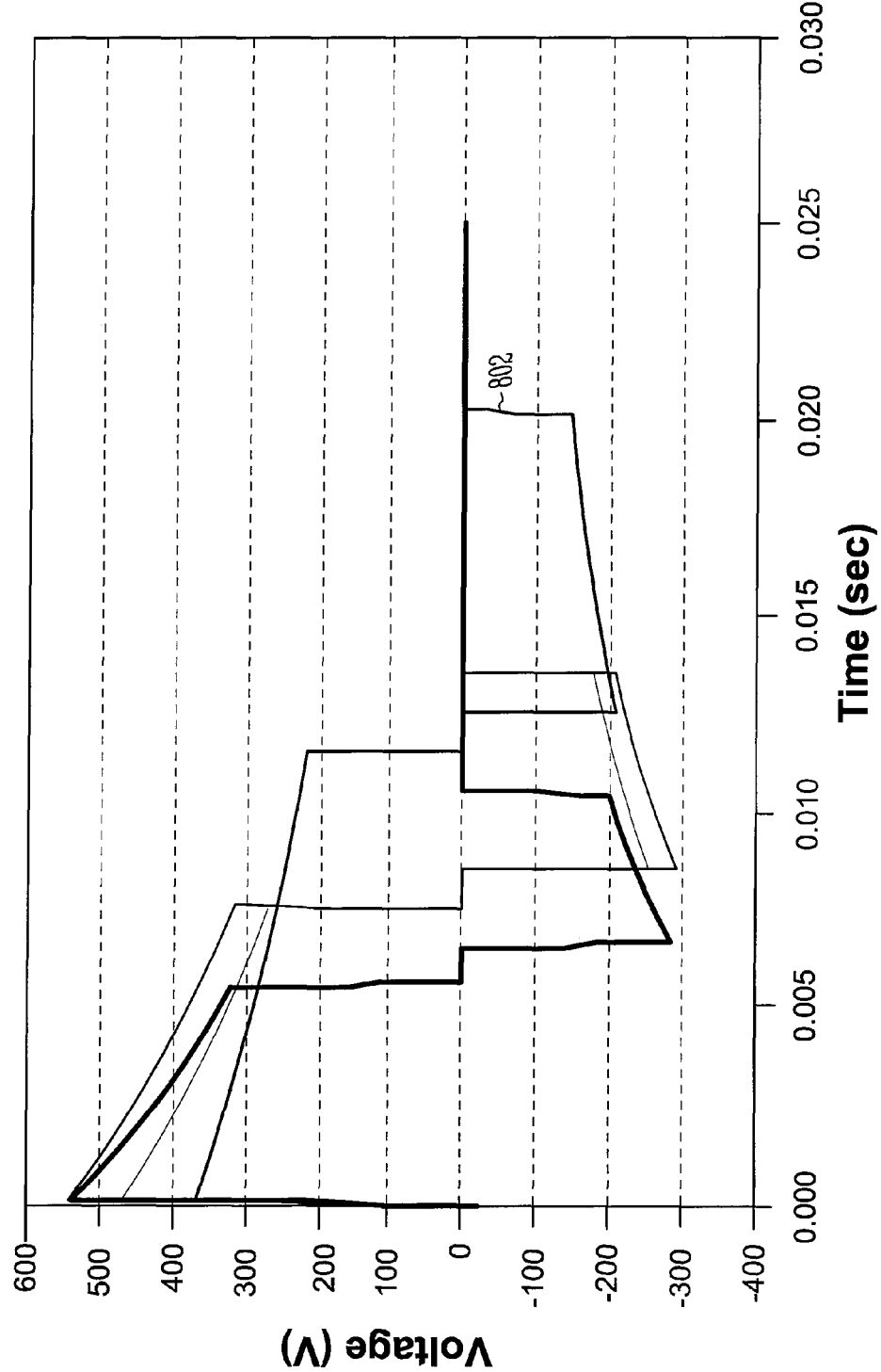
FIG. 8 shows various capacitor wave forms based on a 50 ohm load, according to various embodiments of the present subject matter.
Figure 9:
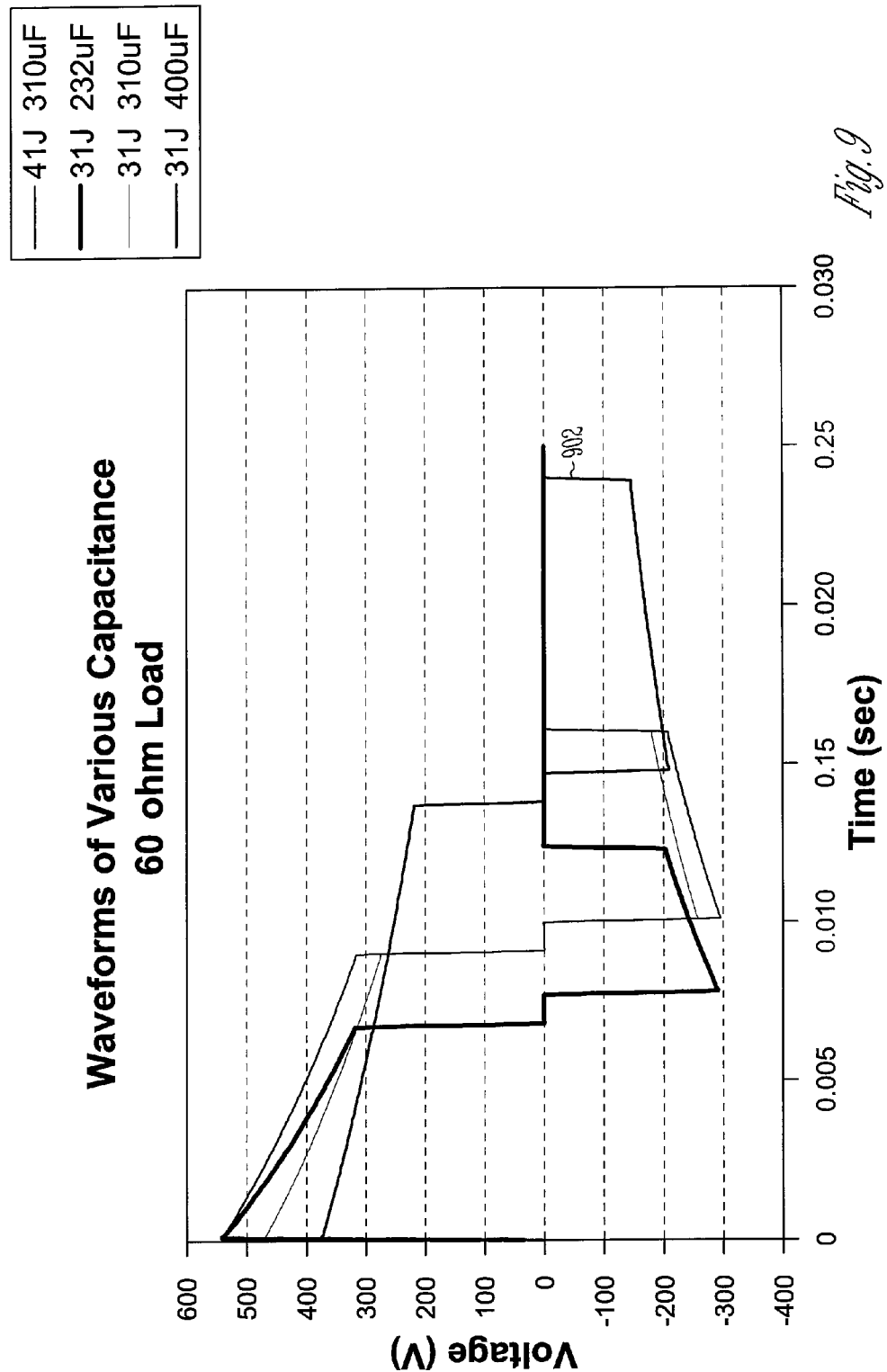
FIG. 9 shows various capacitor wave forms based on a 60 ohm load, according to various embodiments of the present subject matter.

The following table corresponds to FIGS. 7-9. FIG. 7 shows various capacitor wave forms based on a 40 ohm load, according to various embodiments of the present subject matter. An example pulse duration limit 702 is shown for the 31 J 400 µF waveform. FIG. 8 shows various capacitor wave forms based on a 50 ohm load, according to various embodiments of the present subject matter. An example pulse duration limit 802 is shown for the 31 J 400 µF waveform. FIG. 9 shows various capacitor wave forms based on a 60 ohm load, according to various embodiments of the present subject matter. An example pulse duration limit 902 is shown for the 31 J 400 µF waveform. Other impedances not listed herein expressly also fall within the present subject matter.

Some embodiments of the present subject matter include a first capacitor subset having a capacitance of 78 µF. In some of these embodiments, the energy storage of the first capacitor subset is 10 joules. Some of these embodiments include a second capacitor subset having a capacitance of 232 µF. Some of these embodiments have an energy storage capacity of 31 joules. Accordingly, in some of these embodiments, the first and second capacitor subsets, when connected in parallel, have a capacitance of 310 µF. Some of these embodiments have an energy storage ability of 41 joules. These examples are a capacitor subset of a larger group of variations possible within the scope of the present subject matter.

The table and FIGS. 7-9 show that a 400 µF capacitor charged to 393 volts violates the 0.20 ms design requirement. The table also shows that a pair of capacitors switched in parallel can provide 31 J in a waveform which is shorter than the waveform for a 41 J capacitor. The table shows how the waveform lengths differ depending on impedance. Overall, the parallel configuration which allows an operator to use a first capacitor, a second capacitor or both the first capacitor and the second capacitor in parallel, allows for a wide range of applications with a single device including two capacitors.

TABLE 1

Waveform Duration

| | Waveform Duration - Stored Energy vs. Impedance (515 V) Charge Voltage | | | | | | |
|---|---|---|---|---|---|---|---|
| | 393 V | 447 V | 476 V | 515 V | 515 V | 550 V | 550 V |
| | | | | Capacitor Capacity | | | |
| | 31J- 400 µF | 31J- 310 µF | 31J- 273 µF | 31J- 232 µF | 41J- 310 µF | 31J- 205 µF | 41J- 273 µF |
| 40Ω | 16.5 ms | 13.0 ms | 11.0 ms | 9.9 ms | 13.0 ms | 8.9 ms | 11.6 ms |
| 50Ω | 20.1 ms | 15.8 ms | 15.8 ms | 12.1 ms | 15.8 ms | 10.8 ms | 14.0 ms |
| 60Ω | 23.7 ms | 18.6 ms | 18.6 ms | 14.2 ms | 18.6 ms | 12.7 ms | 16.5 ms |

Various embodiments of the present subject matter include a method which includes implanting an implantable device, including positioning at least a first lead proximal the heart. Various embodiments include measuring a system impedance at the first lead. Embodiments include comparing the discharge time of a first capacitor operating at a first tilt level to a threshold time. Some embodiment query if the discharge time is higher than a threshold time. Some embodiments include, when this condition is met, switching the first capacitor into parallel operation with a second capacitor of the implantable device.

The switches shown and described herein can be implemented using software, hardware, and combinations of software and hardware. As such, the term "switch" is intended to encompass software implementations, hardware implementations, and software and hardware implementations.

In various embodiments, the methods provided above are implemented as a computer data signal embodied in a carrier wave or propagated signal, that represents a sequence of instructions which, when executed by a processor, cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Embodiment of Implantable Defibrillator

Figure 10:
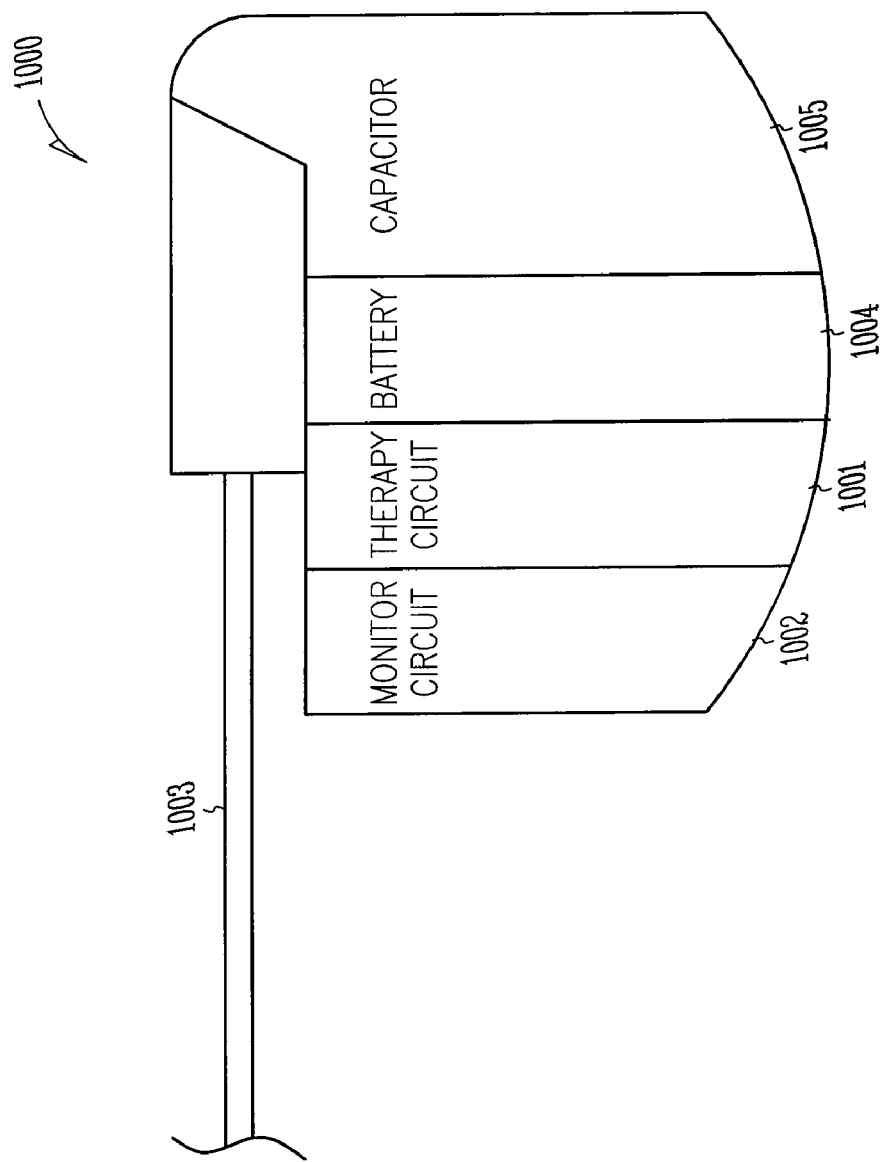
FIG. 10 shows an implantable device, according to one embodiment of the present subject matter.

FIG. 10 shows one of the many applications for capacitors incorporating one or more teachings of the present subject matter: an implantable heart monitor or apparatus 1000. As used herein, implantable heart monitor includes any implantable device for providing therapeutic stimulus to a heart muscle. Thus, for example, the term includes pacemakers, defibrillators, cardioverters, congestive heart failure devices, and combinations and permutations thereof.

Heart monitor 1000 includes a lead system 1003, which after implantation electrically contact strategic portions of a patient's heart. Shown schematically are portions of monitor 1000 including a monitoring circuit 1002 for monitoring heart activity through one or more of the leads of lead system 1003, and a therapy circuit 1001 for delivering electrical energy through one or more of the leads to a heart. Monitor 1000 also includes an energy storage component, which includes a battery 1004 and incorporates at least one capacitor 1005 having one or more of the features of the capacitors described above.

In addition to implantable heart monitor and other cardiac rhythm management devices, one or more teachings of the present subject matter can be incorporated into cylindrical capacitors and/or capacitors used for photographic flash equipment. Teachings of the subject matter are pertinent to any application where high-energy, high-voltage, or space-efficient capacitors are desirable. Moreover, one or more teachings are applicable to batteries.

Figure 11A:
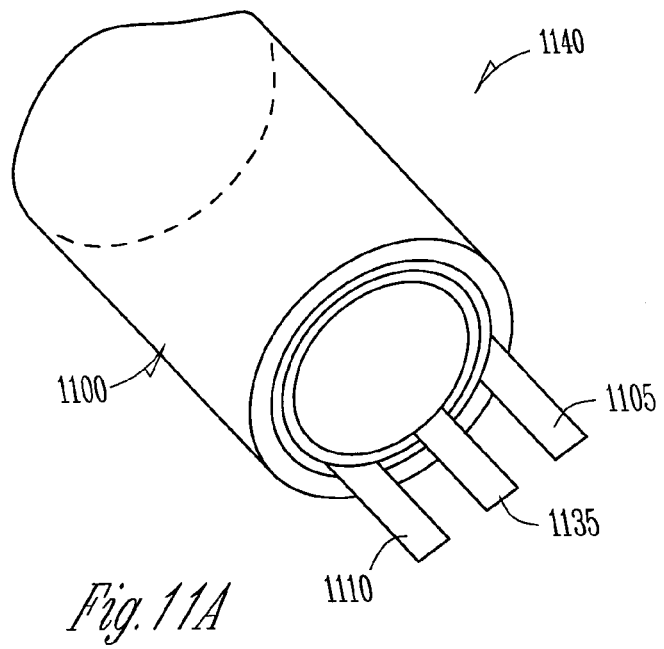
FIG. 11A shows a wound capacitor, according to one embodiment of the present subject matter.

FIG. 11A shows a rolled capacitor, according to one embodiment of the present subject matter. In one embodiment, capacitor 1140 includes a case 1100 for carrying, enclosing, or sealing a spirally wound aluminum electrolytic capacitor, as described below. First anode connection tab 1105, second anode connection tab 1135 and cathode connection tab 1110 provide electrical access to respective first anode, second anode and cathode terminals of capacitor 1140.

Figure 11B:
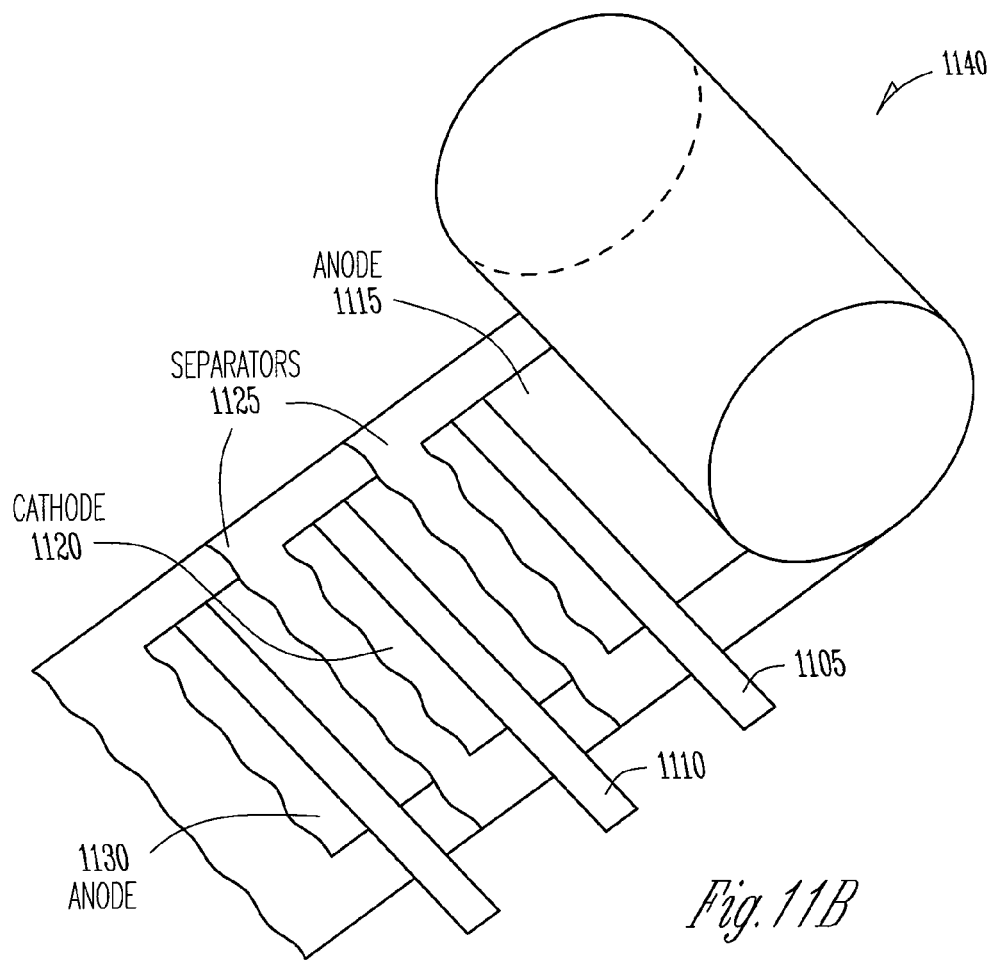
FIG. 11B shows a partially wound capacitor, according to one embodiment of the present subject matter.

FIG. 11B shows a partially rolled capacitor, according to one embodiment of the present subject matter. First anode connection tab 1105 physically and electrically contacts portions of a first anode 1115. In various embodiments, the first anode 1115 includes multiple anode layers which are stacked and which are in contact with one another. In various embodiments, the first stack of anode layers includes anode layers which are electrically interconnected. In various embodiments, these layers are strip shaped. In some embodiments, the layers are ribbon shaped. Second anode 1130 connection tab 1135 physically and electrically contacts portions of a second anode 1130. In various embodiments, the second anode 1130 includes multiple anode layers which are stacked and which are in contact with one another. In various embodiments, the second stack of anode layers includes anode layers which are electrically interconnected. In various embodiments, these layers are strip shaped. In some embodiments, the layers are ribbon shaped. Cathode connection tab 1110 physically and electrically contacts portions of cathode 1120, in various embodiments. In various embodiments, cathode 1120 is strip shaped. In some embodiments, cathode 1120 is ribbon shaped. One or more separators 1125 isolate cathode 1120 from first anode 1115 and second anode 1130.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. An apparatus, comprising:
   a case;
   a plurality of capacitors disposed in the case, the plurality of capacitors comprising a stack of substantially planar electrodes comprising:
      a first capacitor comprising a first partition disposed in the case and comprising interconnected anodes of the stack of substantially planar electrodes, the anodes coupled to anode connection members that are in alignment to define a substantially planar connection surface inside the case along which the anodes of the first partition are interconnected;
      a second capacitor comprising a second partition disposed in the case, with an electrical insulator disposed between the first partition and the second partition, the second partition comprising additional interconnected anodes of the stack of substantially planar electrodes, the additional anodes coupled to additional anode connection members that are in alignment to additionally define the substantially planar connection surface inside the case, wherein the additional interconnected anodes of the second partition are electrically isolated, within the case, from the interconnected anodes of the first partition; and cathodes electrically interconnected and interspersed among the first partition and the second partition, with the first partition having a first capacitance and the second partition having a second capacitance different than the first capacitance;

an electrolyte disposed in the case and contacting the cathodes, the anodes and the additional anodes; and a switching circuit coupled to the first and second partition, the switching circuit adapted to charge the first partition in a first mode and to charge the first partition and the second partition in a second mode, wherein the switching circuit is adapted to provide a variable defibrillation capacitance.

2. The apparatus of claim 1, wherein the case is adapted to fit within an implantable medical device housing.

3. The apparatus of claim 2, wherein the switching circuit is housed in the case with the first partition and the second partition.

4. The apparatus of claim 2, wherein the switching circuit is housed in a compartment of the case separate from the first partition and the second partition.

5. The apparatus of claim 4, wherein the switching circuit is housed adjacent to the first partition and the second partition.

6. The apparatus of claim 2, wherein the switching circuit is switchable from outside the implantable medical device via wireless communication.

7. The apparatus of claim 2, wherein the switching circuit is switchable from outside a human body in which the device is implanted via wireless communication.

8. The apparatus of claim 1, wherein the switching circuit comprises a field effect transistor (FET) adapted to have a source connected to the first capacitor and a drain connected to the second capacitor;

a bipolar junction transistor (BJT) adapted to have an emitter connected to the source of the FET and a collector connected to a gate of the FET;

a first current source connected to the collector of the BJT, wherein activating the first current source turns the FET on, connecting the first and second capacitors; and a second current source connected to a base of the BJT, wherein activating the second current source turns the FET off, isolating the first and second capacitors.

9. The apparatus of claim 8, wherein the stack includes a common cathode which is shared by the first and second capacitor.

10. The apparatus of claim 8, further comprising:
a diode adapted to connect the source of the FET to the drain of the FET, the diode adapted to conduct during discharge of the second capacitor.

11. The apparatus of claim 8, further comprising:
a diode adapted to connect the collector of the BJT to the emitter of the BJT.

12. The apparatus of claim 8, further comprising:
a resistor adapted to connect the base of the BJT to the emitter of the BJT, wherein a resistance value of the resistor is selected to prevent the BJT from turning on due to off-state leakage current from the second current source.

13. The apparatus of claim 1, wherein the first capacitor is adapted to store around 31 Joules, and the second capacitor is adapted to store around 10 Joules.

14. An apparatus, comprising:
a case;
a plurality of capacitors disposed in the case, the plurality of capacitors comprising a stack of substantially planar electrodes comprising:
a first capacitor element disposed in the case and comprising interconnected anodes of the stack of substantially planar electrodes, the anodes coupled to anode connection members that are in alignment to define a substantially planar connection surface inside the case along which the anodes of the first capacitor element are interconnected;

a second capacitor element disposed in the case, with an electrical insulator disposed between the first capacitor element and the second capacitor element, and comprising additional interconnected anodes of the stack of substantially planar electrodes, the additional anodes coupled to additional anode connection members that are in alignment to additionally define the substantially planar connection surface inside the case, wherein the additional interconnected anodes of the first capacitor element are electrically isolated, within the case, from the anodes of the first capacitor element; and cathodes electrically interconnected and interspersed among the first capacitor element and the second capacitor element, with the first capacitor element having a first capacitance and the second capacitor element having a second capacitance smaller than the first capacitance;

an electrolyte disposed in the case and contacting the cathodes, the anodes and the additional anodes;

a charger; and a switching circuit adapted to couple the first capacitor to the charger in a first mode and to couple the first capacitor and the second capacitor to the charger in a second mode;

wherein the switching circuit is adapted to selectively charge the first and second capacitors for use in a defibrillator.

15. The apparatus of claim 14, wherein the charger includes a flyback capacitor charger.

16. The apparatus of claim 14, wherein the switching circuit comprises:
a field effect transistor (FET) adapted to have a source connected to the first capacitor and a drain connected to the second capacitor;

a bipolar junction transistor (BJT) adapted to have an emitter connected to the source of the FET and a collector connected to a gate of the FET;

a first current source connected to the collector of the BJT, wherein activating the first current source turns the FET on, connecting the first and second capacitors; and a second current source connected to a base of the BJT, wherein activating the second current source turns the FET off, isolating the first and second capacitors.

17. The apparatus of claim 16, wherein the stack includes a common cathode which is shared by the first and second capacitor.

18. The apparatus of claim 16, further comprising:
a diode adapted to connect the source of the FET to the drain of the FET, the diode adapted to conduct during discharge of the second capacitor.

19. The apparatus of claim 16, further comprising:
a diode adapted to connect the collector of the BJT to the emitter of the BJT.

20. The apparatus of claim 16, further comprising:
a resistor adapted to connect the base of the BJT to the emitter of the BJT, wherein a resistance value of the resistor is selected to prevent the BJT from turning on due to off-state leakage current from the second current source.

21. An implantable apparatus, comprising:
a case;
a stack of substantially planar electrodes including cathodes and anodes, with the anodes partitioned into a first capacitor partition disposed in the case and comprising interconnected anodes, and a second capacitor partition disposed in the case and comprising additional interconnected anodes, with an electrical insulator disposed between the first capacitor partition and the second capacitor partition, wherein the first partition has a first capacitance and the second partition has a second capacitance smaller than the first capacitance, with the first capacitor partition including a plurality of connection members in alignment to define a substantially planar connection surface inside the case along which the plurality of connection members are interconnected, and with the second capacitor partition including an additional plurality of connection members to additionally define the substantially planar connection surface inside the case, wherein the additional plurality of interconnected plurality of connection members are electrically isolated, within the case, from the anodes of the first partition;
an electrolyte disposed in the case and contacting the cathodes and the anodes; and
a switching circuit coupled to the first capacitor partition and second capacitor partition, the switching circuit adapted to charge the first capacitor partition in a first state and to charge the first capacitor partition and the second capacitor partition in a second state.

22. The apparatus of claim 21, wherein the stack includes a common cathode which is shared by the first capacitor partition and the second capacitor partition.

23. The apparatus of claim 21, wherein a first defibrillation capacitance of the implantable apparatus is equal to the first capacitance of the first capacitor partition and a second defibrillation capacitance of the implantable apparatus is equal to a sum of the capacitance of the first capacitor and the second capacitance of the second capacitor partition.

* * * * *